United States Patent
Uriol Rivera

(10) Patent No.: US 11,464,791 B2
(45) Date of Patent: Oct. 11, 2022

(54) USE OF PARICALCITOL IN THE TREATMENT OF INFLAMMATORY ANAEMIA

(71) Applicant: Miguel Giovanni Uriol Rivera, Islas Baleares (ES)

(72) Inventor: Miguel Giovanni Uriol Rivera, Islas Baleares (ES)

(*) Notice: Subject to any disclaimer, the term of this patent is extended or adjusted under 35 U.S.C. 154(b) by 0 days.

(21) Appl. No.: 15/117,896

(22) PCT Filed: Jan. 16, 2015

(86) PCT No.: PCT/EP2015/050817
§ 371 (c)(1),
(2) Date: Aug. 10, 2016

(87) PCT Pub. No.: WO2015/121022
PCT Pub. Date: Aug. 20, 2015

(65) Prior Publication Data
US 2016/0367571 A1 Dec. 22, 2016

(30) Foreign Application Priority Data
Feb. 11, 2014 (ES) ............... ES201430177

(51) Int. Cl.
*A61K 31/592* (2006.01)
*A61K 38/18* (2006.01)
*A61K 45/06* (2006.01)

(52) U.S. Cl.
CPC ........ *A61K 31/592* (2013.01); *A61K 38/1816* (2013.01); *A61K 45/06* (2013.01)

(58) Field of Classification Search
CPC .............. A61K 2300/00; A61K 31/592; A61K 38/1816; A61K 45/06; A61P 43/00; A61P 7/00; A61P 7/06
USPC ....................................................... 514/169
See application file for complete search history.

(56) References Cited

U.S. PATENT DOCUMENTS

2005/0054620 A1   3/2005   Koeffler et al.

FOREIGN PATENT DOCUMENTS

WO        2004062620 A2    7/2004

OTHER PUBLICATIONS

Dobrez et al. (Nephrol Dial Transplant (2004) 19:1174-1181).*
Teng et al. (The New England Journal of Medicine, 2003;349:446-56).*
Hamad et al. (Use of Intravenous Paricalcitol in Peritoneal Dialysis Patients Improved Control of Secondary Hyperparathyroidism, Journal of Peritonial Dialysis International, Jun. 2007 27:S16, Poster presentation).*
A. Icardi et al. (Nephrol Dial Transplant (28 (7), 1672-Jul. 9, 2013).*
Icardi, Andrea; "Renal anaemia and EPO hyporesponsiveness associated with vitamin D deficiency: the potential role of inflammation," Nephrol. Dial. Transplant., 2013, pp. 1672-1679, vol. 28.
Rivera, Miguel Uriol, et al.; "Influence of the Use of Vitamin D Analogs in the Eritrhopoietic Response to C.E.R.A. in Patients not on Dialysis Previously Treated with EPO," ERA EDTA Congress, 2010, http://www.eraedta2010.org, XP055171698.
Shuja, Suhail B., et al.; "Severe Hyperparathyroidism Despite Paricalcitol Therapy: One-Year Follow-Up," Advances in Peritoneal Dialysis, 2003, pp. 231-235, vol. 19.
Albitar, S., et al.: "High-dose alfacalcidol improves anaemia in patients on haemodialysis," Nephrology Dialysis Transplantation, 1997, pp. 514-518, vol. 12.
Goicoechea, M., et al.; "Intravenous Calcitriol Improves Anaemia and Reduces the Need for Erythropoietin in Haemodialysis Patients," Nephron, 1998, pp. 23-27, vol. 78.
Capuano, Alfredo, et al.; "Beneficial effects of better control of secondary hyperparathyroidism with paricalcitol in chronic dialysis patients," J. Nephrol., 2009, pp. 59-68, vol. 22.
Riccio, Eleonora, et al.; Effects of Paricalcitol on Hemoglobin levels in CKD Patients: A Pilot Randomized Trial, ERA-EDTA 50th Congress, 2013, p. 214.
International Search Report/Written Opinion, dated Mar. 5, 2015.
Grzegorzewska, Alicja E., et al.; "Differences in Clinical and Laboratory Data of Peritoneal Dialysis Patients Selected According to Body Mass Index," Advances in Peritoneal Dialysis, 2003, pp. 222-226, vol. 19.
Avram, Morrell M., et al.; "Importance of Low Serum Intact Parathyroid Hormone as a Predictor of Mortality of Hemodialysis and Peritoneal Dialysis Patients: 14 Years of Prospective Observation," American Journal of Kidney Diseases, 2001, pp. 1351-1357, vol. 38.
Jean, G., et al.; "Association between Very Low PTH Levels and Poor Survival Rates in Haemodialysis Patients: Results from the French ARNOS Cohort," Nephron Clin Pract, 2011, pp. C211-c216, vol. 118.
Phelan, Paul J., et al.; "The Importance of Serum Albumin and Phosphorous as Predictors of mortality in ESRD Patients," Renal Failure, 2008, pp. 423-229, vol. 30.

(Continued)

*Primary Examiner* — Sabiha N Qazi
(74) *Attorney, Agent, or Firm* — Tristan A. Fuierer; Casimir Jones, S.C.

(57) ABSTRACT

The present invention discloses the use of paricalcitol, a synthetic Vitamin D analogue, in the treatment of inflammatory anaemia, preferably in combination with erythropoeisis-stimulating agents. The use of paricalcitol in the treatment of said pathology is associated with a reduced requirement for erythropoeisis-stimulating agents, with optimised iron absorption and with an increase in plasma erythropoietin levels in said patients. The present invention also discloses pharmaceutical compositions that comprise paricalcitol in combination with erythropoeisis-stimulating agents and pharmaceutically acceptable excipients, in addition to the use thereof as drugs in the treatment of inflammatory anaemia.

1 Claim, 14 Drawing Sheets

(56) References Cited

OTHER PUBLICATIONS

Alves, Filipa Caeiro, et al.; "The higher mortality associated with low serum albumin is dependent of systemic inflammation in end-stage kidney disease," PLOS ONE, 2018, vol. 13; e0190410. https://doi.org/10.1371/journal.one.0190410.

Lee, Kyung Hee, et al.; "Low prealbumin levels are independently associated with higher mortality in patients on peritoneal dialysis," Kidney Research and Clinical Practice, 2016, pp. 169-175, vol. 35.

Cohen, Lewis M., et al.; "Predicting Six-Month Mortality for Patients Who are on Maintenance Hemodialysis," Clinical Journal of American Society of Nephrology, 2010, pp. 72-79, vol. 5, doi: 10.2215/CJN.03860609.

Riccio, Eleonora, et al.; "Effect of Paricalcitol vs Calcitriol on Hemoglobin Levels in Chronic Kidney Disease Patients: A Randomized Trial," PLOS ONE, 2015, vol. 10, e-118174, doi:10.1371/journal.pone.0118174.

Alon, Dora Ben, et al.; "Novel role of 1,25(OH)2D3 in induction of erythroid progenitor cell proliferation," Experimental Hematology, 2002, pp. 403-409, vol. 30.

Jelkmann, Wolfgang, et al.; "Regulation of erythropoietin production," J Physiol, 2011, 589 (Pt 6): 1251-1258.

\* cited by examiner

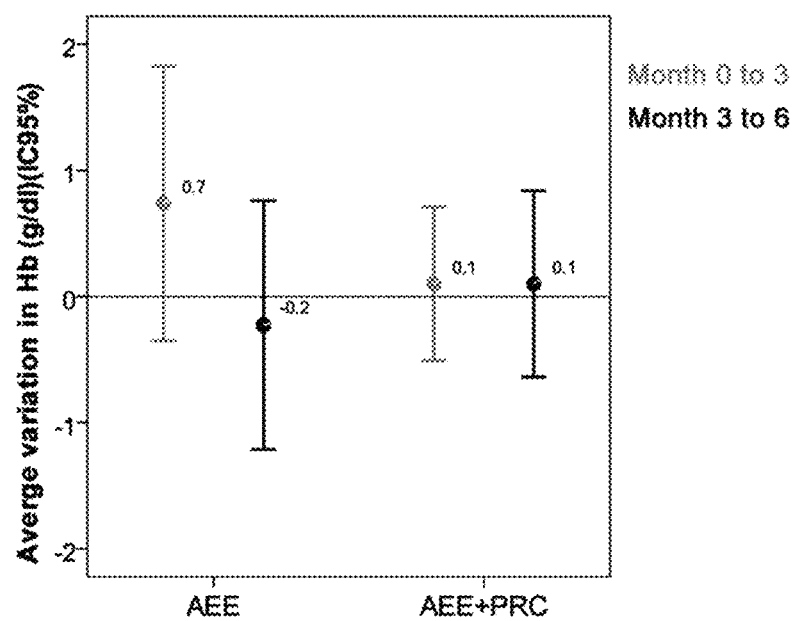

USE OF PARICALCITOL IN THE TREATMENT OF INFLAMMATORY ANAEMIA

CROSS-REFERENCE TO RELATED APPLICATIONS

This application is filed under the provisions of 35 U.S.C. § 371 and claims the priority of International Patent Application No. PCT/EP2015/050817, filed on 16 Jan. 2015 entitled "USE OF PARICALCITOL IN THE TREATMENT OF INFLAMMATORY ANAEMIA" in the name of Miguel Giovanni URIOL RIVERA, which claims priority to Spanish Patent Application No. P201430177 filed on 11 Feb. 2014, both of which are hereby incorporated by reference herein in their entirety.

FIELD OF THE INVENTION

The present invention falls within the field of medicine in general and, more specifically, in the field of treatment of inflammatory anaemia. In particular, the present invention defines the use of paricalcitol, a selective Vitamin D receptor activator, in the treatment of said pathology.

STATE OF THE ART

Inflammatory anaemia, also known as anaemia of inflammation, is a frequent complication in different pathologic entities accompanied by manifest inflammatory processes, mainly chronic, although it is also associated with acute critical illness, cancer or ageing. Its main mechanism is due to a blockage of iron by the high circulatory levels of hepcidin due to hepcidin gene promoter stimulation by IL-6 released during inflammatory process, giving rise to functional iron deficiency and a deficient production of erythropoietin (EPO), in addition to exaggerated red blood cell destruction.

Hepcidin acts by causing the degradation of ferroportin, main iron exporter from cytoplasmic storage to the blood stream, thereby blocking duodenal iron absorption and the release of iron from macrophages, which remains trapped in the interior thereof. This limits iron availability for haemoglobinisation of erythroblasts. Reduced erythropoiesis also contributes to inflammatory anaemia both by direct action and by reducing the synthesis of erythropoietin, as well as increased resistance to its action, due to different cytokines, together with reduced red blood cell lifespan.

The presence of inflammatory anaemia is a factor associated to a worse prognosis within the different chronic pathologies, this relationship being clear in entities such as heart failure, neoplasms, respiratory diseases and chronic kidney disease (CKD), inter alia, and its presence adds a high economic impact to the treatment of the groups of patients who suffer from this disease.

Within the inflammatory situation, the presence of levels of certain pro-inflammatory cytokines (IL-6, IL-1β, TNFα and INFγ, inter alia) has been associated with the development of inflammatory anaemia. In this connection, different treatments aimed at inhibiting and/or neutralising said inflammatory markers such as, for example, tocilizumab, IL-6 receptor inhibitor or infliximab and/or etanercept, TNFα inhibitors, have been used as a therapy aimed at rheumatological diseases such as rheumatoid arthritis. These treatments have been associated with a good response to the inflammatory anaemia developed by patients suffering from said pathology, due to which the inhibition or neutralisation of high levels of these cytokines would improve inflammatory anaemia. Furthermore, the possible anti-inflammatory action of Vitamin D is also known, as well as its analogues and/or precursors. In this connection, Vitamin D receptor activation has been associated with the inhibition of different inflammatory markers (IL-6, IL-1β, INFγ and TNFα).

The administration of Vitamin D and its synthetic analogues has been related in observational studies to an improvement in the erythropoietic response of patients suffering from inflammatory anaemia of chronic kidney disease (CKD) who are being treated with erythropoiesis-stimulating agents (ESA) (Capuano A. et al., J Nephrol 2009; 22:59-68; Albitar S, et al., Nephrol Dial Transplant 1997; 12:514-8; Shuja S B, et al., AdvPerit Dial 2003; 19:231-5; Goicoechea M, et al., Nephron 1998; 78:23-7). This beneficial effect would be directly related to the control of secondary hyperparathyroidism manifested by said patients.

Anaemia in CKD shares physico-pathogenic mechanisms similar to those of inflammatory anaemia. Patients with CKD frequently present the inflammatory condition is frequent, which is associated to the reduced synthesis of EPO and to a deficient response thereto. The physiopathology of CKD is common to that of anaemia in other types of patients, such as those with heart failure, and also shares similarities in terms of overexpression of other cytokines such as IL-1β and IL-6. The treatment of anaemia in patients with CKD is sustained in the use of ESA and other drugs such as iron supplements. ESAs are the greatest contributors to the global economic cost of managing these patients. Likewise, the use of high doses of ESA has been associated with adverse side effects, such as the development of hypertension or difficulty to control it, ictus, thrombotic phenomena and also increased cardiovascular morbidity. In this connection, the use of ESA and iron supplements for treating inflammatory anaemia has been associated with the development of complications similar to those described in patients with CKD. Therefore, the search for new therapeutic measures capable of increasing the effectiveness of ESAs and safely reduce the doses required, in the treatment of patients with inflammatory anaemia, in addition to the significant impact of the new therapies from an economic viewpoint, is advisable.

As mentioned earlier, various studies, mostly observational, have revealed that the administration of Vitamin D and its synthetic analogues such s calcitriol (Goicoechea et al. Nephron. 1998; 78:23-7), paricalcitol (Shuja S B, et al., AdvPerit Dial 2003; 19:231-5) and alfacalcidol (Albitar S, et al., Nephrol Dial Transplant 1997; 12:514-8) have been related to an improved erythropoietic response in patients with anaemia associated with kidney disease and who are being treated with ESA. It should be noted that said quality is observed after the administration of high doses of Vitamin D analogues in patients with moderate to severe hyperparathyroidism and, additionally, said effects were observed after a period of administration of ESAs of more than one year, which makes said treatment unadvisable due to the side effects associated with such high doses of Vitamin D. It should also be noted that the results shown in said studies in terms of improved erythropoietic response are due to the control of secondary hyperparathyroidism in said patients and not to a specific control of the erythropoietic response.

It is also known that the main limiting factor of the use of calcitriol, a synthetic analogue of 1.25 $(OH)_2$ Vitamin D, is induction of hypercalcemia, hyperphosphatemia and vascular calcification. Furthermore, Shuja S. B. et al. (ASAIO Journal; 2003; 49(2):194) discloses the effects of administering paricalcitol (Zemplar) with respect to the erythropoietic requirement in anaemic patients on haemodialysis. The results disclose that patients treated with a lower dose of paricalcitol (0.1 µg/hd) showed relative resistance to EPO in relation to patients treated with higher doses (>10 µg/hd), the former requiring a higher concentration of EPO in relation to the second. It should be noted that the beneficial effects of treatment of anaemia with paricalcitol in patients with CKD on haemodialysis, shown in this study, are not actually due to the reduced requirement of EPO produced by paricalcitol, but rather, as can be observed in said study, said improvement in EPO needs is due, on the one hand, to a poor nutritional status (Group A) and, on the other, to the control of PTH levels (Group C). Group A patients have PTH levels of less than 150 pg/mL, which are normal levels in patients with a poor nutritional status, due to which the higher EPO requirements would be due to said poor nutritional status. Further, Group C patients have PTH levels of 1037 pg/mL, giving rise to severe hyperparathyroidism, due to which the benefit over anaemia in this last group would be attributable to the control of PTH levels. For said reasons, it cannot be considered that the treatment with paricalcitol in said study reveals a beneficial effect in the erythropoietic response. Moreover, the paricalcitol doses used by Shuja S. B. et al. are very high (>10 µg/dialysis, which is equivalent to a weekly average of 30 µg/week) and are also associated with high calcium levels (9.8 mg/dl) which exceed the maximum levels recommended in international guidelines.

Further, Riccio E et al., (50th ERA-EDTA Congress, Istanbul (Turkey). May 2013) disclose that oral administration of paricalcitol improves haemoglobin (Hb) levels in patients with EKD, although it does not make any reference to a reduced need for ESAs in said patients. Worth noting in this study, on the one hand, is that the group of patients treated with paricalcitol reduced PTH levels from 147 pg/mL to 93 pg/mL (nearly 40% with respect to the basal level), compared to a variation in PTH levels from 146 pg/mL to 142 pg/mL (3%) in the control group, due to which it seems that the beneficial effect of the treatment with paricalcitol could be the consequence of the reduction in PTH levels, as described in the state of the art. Further, it should also be noted that the authors of said study mention that the increase in haemoglobin levels in patients treated with paricalcitol is due to the direct stimulation of erythroid precursors, without providing evidence of said claim, particularly when the benefit over erythroid precursors is described in the state of the art for the treatment with calcitriol, which is the group that reduced its average haemoglobin levels, making the conclusion of said study incoherent.

Therefore, as disclosed in the previous studies, treatment with paricalcitol, in terms of the reduced requirement of ESAs in the treatment of inflammatory anaemia is due to the control exerted over secondary hyperparathyroidism. Additionally, the different forms of Vitamin D used in the treatment of inflammatory anaemia seem to be associated with different effects on anaemia and iron metabolism, as demonstrated in the study by Riccio E. et al. (ERA-EDTA 50TH Congress, Istanbul (Turkey). May 2013).

Therefore, there is no consensus on the state of the art for the effective treatment of inflammatory anaemia through the use of Vitamin D or analogues/agonists thereof. Moreover, even the current 2012 KDIGO guidelines (Kidney Disease: Improving Global Outcomes) on anaemia management (KDIGO Clinical Practice Guidelines for Anaemia in Chronic Kidney Disease) do not recommend adjunct treatment with Vitamin (2D evidence) in patients being treated with ESA, in the management and treatment of anaemia in kidney disease (KDIGO); due to which its use is not habitual.

In this connection, the present invention proposes, as opposed to that described in the state of the art, the use of paricalcitol in the treatment of inflammatory anaemia, demonstrating that said compound is capable of reducing the levels of inflammatory markers such as IL-6, in addition to plasma hepcidin levels, improving iron availability through the release thereof from cellular deposits, giving rise to an increase in free plasma iron and a progressive reduction in plasma ferritin levels. Further, the present invention discloses that the use of paricalcitol is associated with higher levels of transferrin saturation index (TSI), as a result of the greater mobilisation of iron from the cellular deposits, due to which the erythroid precursors have a greater iron supply, thereby reducing the concentration of ESAs required to obtain optimum erythropoietic response, as well as inducing greater synthesis of erythropoietin, which in turn would give rise to a decrease in ESA supply. Therefore, the present invention demonstrates that the administration of paricalcitol to patients with inflammatory anaemia reduces ESA requirements in said patients due to optimised iron absorption and to an increase in plasma EPO levels and decrease in inflammatory markers.

DESCRIPTION OF THE INVENTION

Brief Description of the Invention

In order to overcome the problems existing in the state of the art in relation to the provision of an effective treatment for patients with inflammatory anaemia, the present invention describes the use of paricalcitol in the treatment of said pathology, associated with reduced ESA requirements, optimised iron absorption, stabilisation of Hb levels, increased plasma EPO levels and decrease in inflammatory markers in said patients.

Paricalcitol (CAS: 131918-61-1) is a synthetic Vitamin D analogue that is marketed under the brand name Zemplar by Abbvie Laboratories. It is a compound which, to date, has been used mainly in the prevention and treatment of secondary hyperparathyroidism (excessive secretion of the parathyroid hormone) associated with chronic kidney disease. Chemically, is the compound 19-nor-1, 25-(OH) 2-vitamin D2 or 19-nor-1.25-dihydroxyvitamin D2, being an analogue of 1.25-dihydroxycholecalciferol, the active form of Vitamin D2 (ergochalciferol). Its chemical structure is:

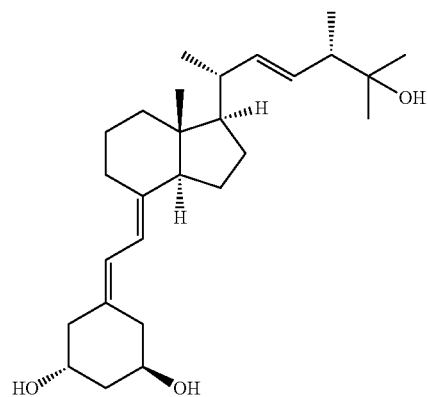 [SMILES: C[C@H](/C=C/[C@H](C)C(C)(C)O)[C@H]1CC[C@H]2/C(=C/C=C3C[C@@H](O)C[C@H](O)C3)CCC[C@]12C]

Specifically, the present invention discloses the use of paricalcitol in the manufacture of a pharmaceutical composition for the treatment of inflammatory anaemia, preferably wherein the paricalcitol dose is comprised between 5-10 µg/week. Alternatively, the present invention discloses paricalcitol at a preferred dose of between 5-10 µg/week, for use in the treatment of inflammatory anaemia.

For the purposes of the present invention, inflammatory anaemia is defined as a pathology that presents iron deficiency due to a deregulation in the inflammatory system. The diseases that are usually associated with inflammatory anaemia are, for example, chronic kidney disease, cancer, infectious diseases, etc. Subjects with inflammatory anaemia cannot absorb iron effectively to produce new red blood cells, even if the amount of iron stored in the body's tissues is normal or even high, with the resulting tissue damage. As a result, the number of new healthy red blood cells gradually decreases. Similarly, the amount of haemoglobin, the component of the red blood cells that carries oxygen to body tissues and muscles, also decreases.

Paricalcitol, as described throughout the present invention, for use in the treatment of inflammatory anaemia, can be used in combination with erythopoiesis-stimulating agents. The administration of said agents with paricalcitol for treating inflammatory anaemia can be combined, simultaneous or sequential. Additionally, as demonstrated throughout the present invention, patients with inflammatory anaemia being treated with ESAs have a lower requirement of said compounds when they are administered paricalcitol, with the advantages entailed by said reduced ESA requirement, mainly associated with the side effects of said ESAs.

For the purposes of the present invention, the erythropoiesis-stimulating agents are defined as those agents or compounds similar to erythropoietin capable of stimulating erythropoietic processes, which are responsible for producing erythrocytes. ESAs include natural erythropoietin or EPO and synthetic ESAs, whose chemical structure is similar to that of EPO and are capable of producing the same biological effects as EPO. The synthetic ESAs described in the state of the art include, most notably:

First-generation ESAs: Epoetina alfa (CAS No.: 113427-24-0): Eprex, Epopen; Epocept, Nanokine, Epofit, Epogin, Binocrit, Procrit; Epoietin beta (CAS No.: 122312-54-3): Neorecormon, Recormon; Epoietin delta (CAS No.: 0261356-80-3): Dynepo; Epoietin zeta (CAS No: 0604802-70-2).

Second-generation ESAs: Darbepoietin alfa (Aranesp) (CAS No.: 11096-26-7).

Third-generation ESAs: CERA: "Continuous erythropoietin receptor activator" (Mircera).

Another object disclosed in the present invention relates to a pharmaceutical composition comprising paricalcitol, preferably for being administered to patients who require it, at a dose comprised between 5-10 µg/week, in combination with ESAs and together with pharmaceutically acceptable excipients or vehicles.

In a preferred embodiment, the composition of the invention can also comprise another active ingredient. In a more preferred embodiment, said active ingredients are preferably iron supplements.

Another object disclosed in the present invention relates to the previously described pharmaceutical composition for use as a drug or, alternatively, relates to the use of the composition of the invention in the manufacture of a drug.

Another object disclosed in the present invention relates to the previously described pharmaceutical composition for use in the treatment of inflammatory anaemia or, alternatively, relates to the use of the composition of the invention in the manufacture of a drug for treating inflammatory anaemia.

Another object disclosed in the present invention relates to a method for treating inflammatory anaemia, characterised in that paricalcitol is administered to a subject with said disease at a dose comprised between 5-10 µg/week or a pharmaceutical composition as described in the present invention.

The content of all the aforementioned references, including the patents cited throughout this document and references enumerated below, have been expressly included with reference to this application. In the event of conflict, the definitions included in this document shall prevail.

DESCRIPTION OF THE DRAWINGS

FIG. 27 shows the variation in Hb levels (g/dl) expressed as median±DE during months 0-3 (grey lines) and months 3-6 (black lines) in the group of patients being treated without paricalcitol (0.73±1.30 and −0.22±1.17 g/dl, p=0.25, n=8) and in the group of patients receiving combined treatment (ESA+PRC): (0.10±0.14 and 0.10±1.70 g/dl, p=0.99, n=23).

DETAILED DESCRIPTION OF THE INVENTION

Figure 1:
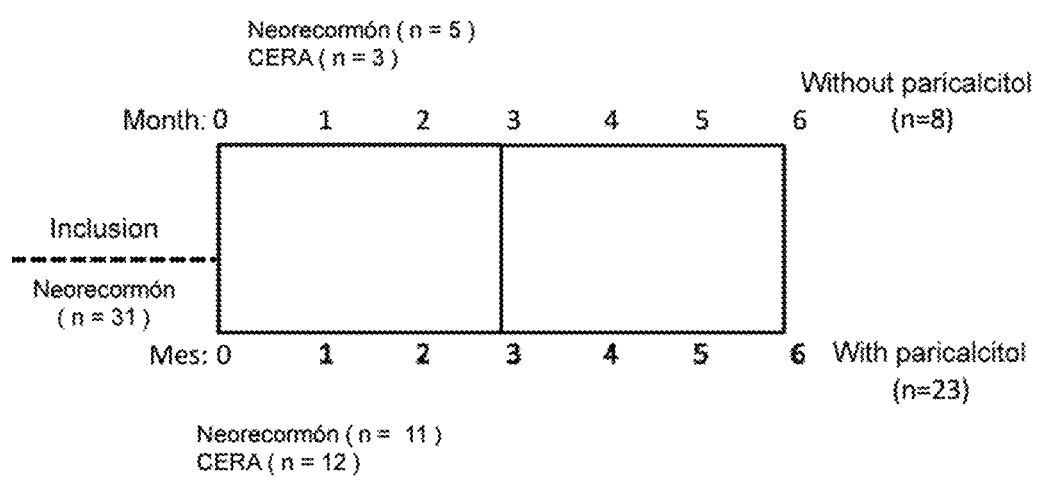
FIG. 1 shows the MIR-EPO study (Study A). ESAs: Neorecormon and CERA. The three first months (months 0-3) correspond to the ESA dose titration phase and the three remaining months (months 3-6) correspond to the ESA dose maintenance phase (n: number of patients included in each group).

One of the objects of the present invention relates to the use of paricalcitol in the manufacture of a pharmaceutical composition for the treatment of inflammatory anaemia, wherein the dose of paricalcitol to be administered is comprised between 5-10 µg/week, preferably the dose of paricalcitol to be administered is 1 µg/day and, more preferably, the dose of paricalcitol to be administered is 5 µg, twice a week. Alternatively, the present invention in turn describes paricalcitol, to be administered at a dose comprised between 5-10 µg/week, for use in the treatment of inflammatory anaemia. Preferably, the dose of paricalcitol to be administered, for use in the treatment of inflammatory anaemia, is 1 µg/day and, more preferably, the dose of paricalcitol to be administered is 5 µg, twice a week.

In another preferred embodiment, paricalcitol may be used, at the dose indicated above, in combination with at least one erythropoiesis-stimulating agent. The administration of the ESA can be combined, simultaneous or sequential in relation to the use of paricalcitol.

In another preferred embodiment, the ESAs are selected from among any of the following: EPO, first-generation ESAs: Epoetin alfa (CAS No: 113427-24-0): Eprex, Epopen; Epoetin beta (CAS No: 122312-54-3): Neorecormon; Epoetin delta (CAS No: 0261356-80-3): Dynepo and Epoetin zeta (CAS No: 0604802-70-2); second-generation ESAs: Darbepoetin alfa (Aranesp) (CAS No: 11096-26-7) and/or third-generation ESAs: CERA: "Continuous erythropoietin receptor activator"(Mircera).

In another even more preferred embodiment, the preferred ESA for use in the present invention is selected from among: Epoetin beta, Neorecormon, Epoetin zeta, Darbepoetin alfa and CERA.

Another of the objects described in the present invention related to a pharmaceutical composition comprising paricalcitol, to be administered at a dose comprised between 5-10 µg/week, in combination with at least one ESA and together with pharmaceutically approved vehicles or excipients.

In a preferred embodiment, the dose of paricalcitol comprised in the pharmaceutical composition, to be administered to a patient who requires it, is 1 µg/day. In another preferred embodiment, the dose of paricalcitol to be administered is 5 µg twice a week.

In another preferred embodiment, the ESA present in the composition of the invention is selected from among: EPO, first-generation ESAs: Epoetin alfa (CAS: 113427-24-0): Eprex, Epopen; Epoetin beta (CAS: 122312-54-3): Neorecormon; Epoetin delta (CAS: 0261356-80-3): Dynepo and Epoetin zeta (CAS No: 0604802-70-2); second-generation ESAs: Darbepoetin alfa (Aranesp) (CAS: 11096-26-7) and/or third-generation ESAs: CERA: "Continuous erythropoietin receptor activator" (Mircera), preferring any of the following: Epoetin Beta, Neorecormon, Epoetin zeta, Darbepoetin alfa and CERA.

Another of the objects disclosed in the present invention relates to the previously described pharmaceutical composition, characterised in that it may comprise another active ingredient. In a more preferred embodiment, said active ingredient is preferably, at least, an iron supplement.

Another of the objects disclosed in the present invention relates to the use of the pharmaceutical composition with the doses of paricalcitol described throughout the present invention, in the manufacture of a drug. Alternatively, the present invention also relates to the pharmaceutical composition, with the dose of paricalcitol described throughout the present invention, for use as a drug.

Another of the objects disclosed in the present invention relates to the use of the pharmaceutical composition, with the doses of paricalcitol described throughout the present invention, in the manufacture of a drug for the treatment of inflammatory anaemia. Alternatively, the present invention also relates to the pharmaceutical composition, with the doses of paricalcitol described throughout the present invention, for use as a drug in the treatment of inflammatory anaemia.

As used herein, the term "active ingredient", "active substance", "pharmaceutically active substance", "active ingredient" or "pharmaceutically active ingredient" means any component that potentially provides a pharmacological activity or other different effect in the diagnosis, cure, mitigation, treatment or prevention of a disease, or that affects the structure or function of the human body or that of other animals. The term includes those components that promote a chemical change in the manufacture of the drug and are present therein in an expected modified form that provides the specific activity or effect.

The pharmaceutical compositions of the present invention can be formulated for administration to an animal and, more preferably, to a mammal, including humans, in a variety of forms known in the state of the art. Therefore, they can be, but not limited to, in sterile aqueous solution or in biological fluids such as serum. Aqueous solutions may be buffered or not buffered and have additional active or inactive components. The additional components include salts for modulating the ionic force, preservatives including, but not limited to, antimicrobial agents, antioxidants, chelating agents and similar, and nutrients including glucose, dextrose, vitamins and minerals. Alternatively, the compositions can be prepared for administration in solid form. The compositions can be combined with various inert vehicles or excipient including, but not limited to, binding agents such as microcrystalline cellulose, tragacanth gum or gelatin; excipients such as starch or lactose; dispersing agents such as alginic acid or corn starch; lubricants such as magnesium stearate; sliding agents such as colloidal silicon dioxide; sweetening agents such as sucrose or saccharine; or agents such as mint or methyl salicylate.

Such compositions and/or their formulations can be administered to an animal, including a mammal, and, therefore, to a human, in a variety of forms, including, but not limited to, intraperitoneal, intravenous, intramuscular, subcutaneous, intrathecal, intraventricular, oral, enteral, parenteral, intranasal or dermal. Preferably, the route of administration is oral or intravenous.

The dose for obtaining a therapeutically effective amount depends on a variety of factors such as, for example, the age, weight, sex, tolerance, . . . of the mammal. In the sense used in this description, the expression "therapeutically effective amount" relates to the amount of compounds; in the case of the present invention, it relates to the amount of paricalcitol or accompanying active ingredient, or its salts, pro-drugs, by-products or analogues, or to its combinations, that produce the desired effect and, in general, shall be determined, inter alia, by the characteristics inherent to said pro-drugs, by-products and analogues and the therapeutic effect to be achieved. The "pharmaceutically acceptable adjuncts", "excipients" and "vehicles" that can be used in said compositions are the vehicles known by the persons skilled in the art.

The terms "adjunct", "excipient", "additive" or any of its synonyms, relate to a substance that aids absorption, distribution or action of any of the active ingredients of the present invention, stabilises said active substance or aids the manufacture of the drug in the sense of giving it consistency or adding flavours that make it more pleasant. Therefore, excipients could have the function of binding the ingredients together such as, for example, starches, sugars or celluloses, sweetening function, colouring function, protective function of the drug such as, for example, isolating it from air and/or humidity, filling function of a pill, capsule or any other form of presentation such as, for example, dibasic calcium phosphate, disintegrating function to facilitate the dissolution of the components and their absorption in the intestine, without excluding other types of excipients not mentioned in this paragraph.

The term "pharmaceutically acceptable" relates to the fact that the excipient is permitted and evaluated so that it does not damage the organisms to which it is administered. Additionally, the excipient must be pharmaceutically adequate, i.e. an excipient that allows the activity of the active ingredient or active ingredients, i.e. it must be compatible with the active ingredient; in this case, the active ingredient is paricalcitol.

A "pharmaceutically acceptable" vehicle relates to the substances, or combination of substances, known in the pharmaceutical sector, used in the manufacture of pharmaceutical forms of administration and include, but are not limited to, solids, liquids, solvents or surfactants.

The vehicle, like the excipient, is a substance used in the drug to dilute any of the compounds of the present invention up to a certain volume or weight. The pharmaceutically acceptable vehicle is an inert substance or a substance with an identical action to any of the cells of the present invention. The function of the vehicle is to facilitate the addition of other compounds, allow improved dosing and administration or give consistency and shape to the pharmaceutical composition.

Another of the objects disclosed in the present invention relates to a method for treating inflammatory anaemia characterised in that a dose of paricalcitol comprised between 5-10 µg/week is administered to a subject with said disease, or to the composition of the invention, as described throughout the present document.

In a preferred embodiment, the method of the invention is characterised in that the dose of paricalcitol to be administered is 1 µg/day. In another preferred embodiment, the method of the invention is characterised in that the dose of paricalcitol to be administered is 5 µg twice a week.

In another preferred embodiment, the method of the invention is characterised in that paricalcitol, at the aforementioned doses, may be used in combination with at least one ESA. In an even more preferred embodiment of the invention, the administration of the ESA can be combined, simultaneous or sequential in relation to the use of paricalcitol.

In another preferred embodiment of the method of the invention, it is characterised in that the ESAs are selected from among any of the following: EPO, first-generation ESAs: Epoetin alfa (CAS: 113427-24-0): Eprex, Epopen; Epoetin beta (CAS: 122312-54-3): Neorecormon; Epoetin delta (CAS: 0261356-80-3): Dynepo and Epoetin zeta (CAS No: 0604802-70-2); second-generation ESAs: Darbepoetin alfa (Aranesp) (CAS: 11096-26-7) and/or third-generation ESAs: CERA: "Continuous erythropoietin receptor activator" (Mircera). In another even more preferred embodiment, the preferred ESA for use in the present invention is selected from among: Epoetin beta, Neorecormon, Epoetin theta, Darbepoetin alfa and CERA.

The term "individual" or "subject", as used in the description, relates to animals, preferably mammals and, more preferably, humans. The term "individual" or "subject" is not intended to be limiting in any aspect, and can be of any age, sex and physical condition.

Throughout the description and the claims, the word "comprises" and its variants must be interpreted in an inclusive sense, as opposed to an inclusive or exhaustive sense such as, for example, the term "includes." That is, the term "comprises" must be interpreted in the sense of "includes, but is not limited to," while the term "includes" must be interpreted in the sense of "includes and is limited to." Therefore, the word "comprises" and its variants do not aim to exclude other technical characteristics, components or steps.

For persons skilled in the art, other objects, advantages and characteristics of the invention shall be inferred partly from the description and partly from the practical part of the invention. The following examples and drawings are provided by way of illustration and are not aimed at limiting the present invention.

EXAMPLES

Methods:

For the purpose of evaluating the benefits of the use of paricalcitol in anaemia of inflammatory characteristics, three different studies have been developed. In the first study, the physiopathological benefits of treating patients with anaemia of inflammatory characteristics with paricalcitol were analysed (Study A: MIR-EPO). Additionally, two cross-sectional studies were conducted that confirmed, on the one hand, the optimum doses of paricalcitol (Study B) and, on the other, the differences between two Vitamin D analogues regularly used in clinical practice (calcitriol versus paricalcitol) (Study C).

Description of the Studies:

a) Study A (MIR-EPO Study):

A controlled prospective study in which the evolution of ESA doses, Fe supplement doses, evolution of Fe, of transferrin, of ferritin, of the transferrin saturation index, of the haemoglobin levels and of the non-conventional markers associated with inflammatory anaemia was determined: Hepcidin and IL-6 and analysis of the hormones associated with a improved erythropoietic response. The variability of the haemoglobin was also assessed. A total of 31 patients were included in this study. The ESAs used by the patients were Epoetin beta (Neorecormon) and CERA.

This study is a controlled, observational and analytical prospective-type study of cases and controls. The study lasted six months. In the first three months the ESA dose titrations were obtained and, in the remaining three months corresponded to the maintenance phase. The data shown in the present invention form part of the MIR-EPO Study (EudraCT: 2009-015511-40) https://www.clinicaltrialsregister.eu. The design of the MIR-EPO Study assessed patients being treated with an erythropietic agent (Epoetin-beta-Neorecormon or CERA). In said patients, the differences between the groups with and without paricalcitol were analysed, due to which the results shown in the present invention related specifically to the following groups:

Group of patients being treated with paricalcitol (paricalcitol+ESA), i.e. combined treatment, and Group of patients being treated exclusively with an ESA.

Patients. All the patients signed an informed consent prior to participating in the study, which was approved by the local ethics committee and by the Spanish Agency of Medicines and Medical Devices. A total of 31 patients were included. The patients selected belong to the Chronic Dialysis Unit of the Hospital Universitario Son Espases (HUSE) in Palma de Mallorca and to the Chronic Haemodialysis Unit of the Policlínica Miramar. The baseline characteristics of the patients included in this study are shown in Table 1.

TABLE 1

Clinical characteristics of the patients included in Study A.

| N = 31 | ESA-PRC (n = 8) | ESA + PRC (n = 23) | P-value |
|---|---|---|---|
| Age (years) | 53 ± 18 | 62 ± 16 | 0.24 |
| Time on dialysis (months) | 28 (23-40) | 32 (18-49) | 0.58 |
| IMC (Kg/m$^2$) | 22 (20-31) | 27 (24-33) | 0.15 |
| Hb (g/dl) | 12 ± 0.9 | 11.7 ± 0.8 | 0.43 |
| Kt/v | 1.55 ± 0.2 | 1.55 ± 0.2 | 0.99 |
| PCRn (g/Kg/day) | 0.79 (0.72-1.15) | 1 (0.81-1.0) | 0.29 |
| IST % | 29.7 (23-40) | 26 (21-36) | 0.41 |
| Ferritin (ng/ml) | 650 ± 373 | 873 ± 492 | 0.25 |
| Fe$^{2+}$ (µg/dl) | 66 (53-85) | 71 (52-76) | 0.84 |
| Transferrin (mg/dl) | 170 (133-196) | 156 (144-185) | 0.80 |
| Erythrocyte count (M/µl) | 3.8 ± 0.3 | 3.6 ± 0.2 | 0.42 |
| GSV 1° h (mm) | 16 ± 11 | 38 ± 23 | 0.01 |
| Total cholesterol (mg/dl) | 137 ± 59 | 144 ± 34 | 0.68 |
| Albumin (g/l) | 39.3 ± 2.4 | 39.6 ± 3.8 | 0.85 |
| 25 (OH) Vitamin D (ng/ml) | 27 ± 11 | 22 ± 12 | 0.30 |
| Calcium (mg/dl) | 8.6 ± 0.6 | 9.0 ± 0.6 | 0.13 |
| P (mg/dl) | 4.1 ± 1 | 4.4 ± 1.4 | 0.58 |
| PTHi (pg/ml) | 163 ± 127 | 327 ± 159 | 0.01 |
| Folic acid (ng/ml) | 17.8 ± 14 | 19.4 ± 13.3 | 0.76 |
| Vitamin B12 (pg/ml) | 487 (389-681) | 417 (313-673) | 0.56 |
| Initial Beta-epoetin (UI/week) | 7000 (3250-8500) | 5000 (4000-9000) | 1.00 |
| Fe supplements Yes, n (%) | 7 (87%) | 18 (78%) | 1.00 |

Median ± DE, Median (p25-p75).
Kt/v: Dialysis dose,
nPCR: Normalised Protein Catabolic Rate,
TSI %: Transferrin Saturation Index,
GSV: Globular Sedimentation Velocity,
PTHi: Parathormona intacta.
AAE: Erithropoietin-Stimulating Agent,
PRC: Paricalcitol.
Analysis according to Student T-Test or Mann-Whitney U-Test, as required.

Study inclusion criteria: Patients ≥18 years old, haemodialysis with the same type of filter for the three months prior to inclusion in the study, KT/V ≥1.2 (according to the Dauguirdas second-generation technique), concentration of Hb between 10.5 and 12 g/dl at least for the twelve weeks prior to inclusion in the study, preliminary treatment with stable doses of EPO (beta-epoetin) +/−1000 UI for the twelve weeks prior to the start of the study, transferring saturation ≥20% and serum ferritin level >100 ng/ml.

Study exclusion criteria: Grade IV heart failure (NYHA), active bleeding episode or transfusion history during the study period, non-renal causes of anaemia, neoplasms, folic acid or Vitamin B12 deficiency, haemoglobinopathies, haemolysis, pure red cell aplasia secondary to treatment with erythropoietin, acute or chronic infection or symptomatic or uncontrolled inflammatory disease, poorly controlled hypertension (HTA) requiring the suspension of human recombinant EPO (hrEPO), immunosupressor concomitant treatment with uncontrolled haemoglobin, thrombocytopathies and/or medular aplasia.

ESA dose adjustment protocol: the dose of ESAs was assessed by determining haematimetry on a monthly basis in the two treatment groups, adjusting the dose of ESA according to the protocol four weeks after starting the treatment, or previously if clinically or analytically required, prolonging the study period 24 weeks (FIG. 1).

The dose of ESA will be increased according to the following parameters:
  25% if a decrease in Hb is produced <2 g/dL or if Hb ≥9 and <11 g/dL.
  50% if a decrease in Hb is produced ≥2 g/dL or if Hb is <9 g/dL.
The dose of ESA will be reduced according to the following parameters:
  25% if an increase in Hb is produced ≥1 g/dL or if Hb levels are between 12 and 13 g/dL.
  50% if there is an increase in Hb >2 g/dL.
It will be temporarily suspended for one month and reintroduced reducing 25% the lowest dose of ESA administered, if Hb >14 g/dL.

In order to maintain a safe and appropriate treatment of secondary hyperparathyroidsm, treatment with paricalcitol can be initiated in those patients who require it; however, this will be considered a study exclusion criterion.

The administration of iron supplements shall always be intravenous with the aim of maintaining a transferrin saturation index (TSI %) greater than 20%.

Analytical determinations: all the blood samples were analysed in the central laboratory of the HUSE, applying the methodology regularly used in clinical practice:
  Hb: Haemoglobin was determined on a monthly basis prior to the dialysis session and corresponding weekday. The analysis of the samples was performed using flow cytometry (CELL-DYN Sapphire®—Abbott) at the central laboratory of the HUSE.
  Klotho: Human Soluble α-Klotho Assay Kit—IBL. ELISA (Enzyme-LinkedImmunoSorbentAssay) sandwich type using two types of high-specificity anti-Human Klotho antibodies (67G3 and 91F1). Using TeTraMeltilBenzidina (TMB) as a chromogeneous agent.
  Hepcidin: DGR HepcidinProhormone ELISA kit. ELISA (Enzyme-LinkedImmunoSorbentAssay) of competitive type with anti-Pro-Hepcidin (polyclonal) antibodies.
  IL-6: Quantikine ELISA Human IL-6 immunoassay. ELISA (Enzyme-LinkedImmunoSorbentAssay) sandwich type using specific antibodies for mouse monoclonal and polyclonal IL-6.
  Erythropoietin: Quantikine IVD ELISA Human Erythropoietin Immunoassay. ELISA (Enzyme-LinkedImmunoSorbentAssay) "DAS" sandwich type (DoubleAntibodySandwich) with mouse monoclonal and rabbit polyclonal antibodies against human recombinant erythropoietin.

The non-conventional inflammatory parameters were determined in months 3 and 6 of the study, due to the fact that it is considered that the first three months of the study were dedicated to ESA dose titration and the last three months to the maintenance phase, as mentioned previously. As in the case of blood count determinations, the extractions were made prior to the mid-week dialysis session.

Biobank: In order to analyse inflammatory anaemia markers: IL-6, hepcidin, erythropoietin and plasma Klotho levels, samples obtained and stored according to protocol in the biobank of the HUSE were recovered (Code: PNT/BB/PA/000.01) and that corresponds to months 3 and 6.

b) Study B:

A cross-sectional study designed to assess the differences between calcitriol and paricalcitol associated with the use of ESAs, both used in the treatment of secondary hyperparathyroidism. A total of 92 patients from the Chronic Dialysis Unit of the Hospital Universitario Son Espases (HUSE) in Palma de Mallorca and from the Chronic Haemodialysis Unit of the Policlínica Miramar were included. A total of 31 patients were treated with calcitriol and a total of 61 patients were treated with paricalcitol. The ESA analysed was Epoetin beta (Neorecormon).

The clinical characteristics of the patients included in Study B are shown in Table 2.

TABLE 2

Clinical characteristics of the patients included in Study B.

| N = 92 | Median ± DE | Minimum value | Maximum value |
|---|---|---|---|
| Hb (g/dl) | 16.62 ± 1.3 | 8 | 15 |
| TSI % | 27.6 ± 10.5 | 6 | 54 |
| Ferritin (ng/ml) | 321 (152-625) | 27 | 1455 |
| PTHi (pg/ml) | 299 (190-550) | 20 | 2700 |
| Epoetin-beta (UI/week) | 4000 (2000-5500) | 0 | 19000 |
| Epoetin-beta, Yes/No (n/%) | 76 (83)/16 (17) | | |
| IV Fe supplements, Yes/No, n (%) | 72 (78)/20 (22) | | |

Hb: Haemoglobin,
TSI: Transferrin Saturation Index,
PTHi: Parathormona intacta.
Median ± DE, median (p25-p75).

c) Study C:

A cross-sectional study designed to assess the distribution of the dose of paricalcitol (μg/week) associated with a greater erythropoietic response. That is, the aim is to assess the predictive capacity of the doses of paricalcitol (μg/week) over the doses of ESA (UI/week), in addition to assessing the doses of paricalcitol to predict Hb levels (g/dl) and identify the doses of paricalcitol associated with certain Hb levels in a range between 10 and 12 g/dl, which are the levels considered to be optimum.

A total of 58 patients were included in this study. The ESA analysed was Epoetin beta (Neorecormon). The clinical characteristics of said patients are shown in Table 3. Said Table 3 also shows the comparative results between the group of patients being treated with ESA and those receiving combined treatment (ESA+paricalcitol).

TABLE 3

Baseline characteristics of the patients included in Study C.

| N = 58 | Median ± DE | Minimum value | Maximum value |
|---|---|---|---|
| Age (years) | 60 ± 13 | 23 | 83 |
| Sex (M/F), n (%) | 30 (52)/28 (48) | | |
| Hb (g/dl) | 11.38 ± 1.6 | 7.4 | 15.4 |
| TSI % | 30 ± 11 | 11 | 68 |
| PTHi (pg/ml) | 215 (150-368) | | |
| Paricalcitol (mcg/week) | 5 (0-7) | | |
| Epoetin-beta (UI/week) | 4500 (2000-9250) | | |
| Paricalcitol, Yes/No (n %) | 37 (64)/21 (36) | | |
| Epoetin-beta, Yes/No (n %) | 46 (79)/12 (21) | | |

Median ± DE, median (P25-P75).
PTHi: Parathormona intacta,
TSI: Transferrin Saturation Index,
Hb: Haemoglobin.

Statistical analysis: The results obtained are presented as median±DE expressed as a percentage, as required. The comparison between quantitative variables was performed using the Student T-Test or Mann-Whitney U-Test, according to their distribution. The Chi-Square or Fisher's Exact Test was used to compare the qualitative variables. The comparison between averages recurring throughout the follow-up time was performed using the Student T-Test for related samples or Wilcoxon's Test, according to their distribution, adjusting the point of significance for multiple comparisons. The changes in the variables in the branches of study throughout the study were analysed using a linear model for recurring measurements, with the previous logarithmic transformation to ensure the normal distribution of the sample. In the case of not achieving an adequate normalise distribution, non-parametrical methods shall be used. For the multiple comparison between correlated data pairs, the Bonferroni Correction shall be used. The statistical analysis shall be performed using the statistical software SPSS 18.0 for Windows.

Since two different types of ESAs were used (Epoetin beta and CERA), with the aim of homogenising the result in terms of the need for these drugs, the doses of ESAs were transformed into their percentage values, where 100% of the dose corresponds to point zero (Month 0).

Optimum Doses of Paricalcitol for Obtaining an Improved Erythropoietic Response and Stabilising Plasma Hb Levels (Data Obtained from Study C).

Figure 2:
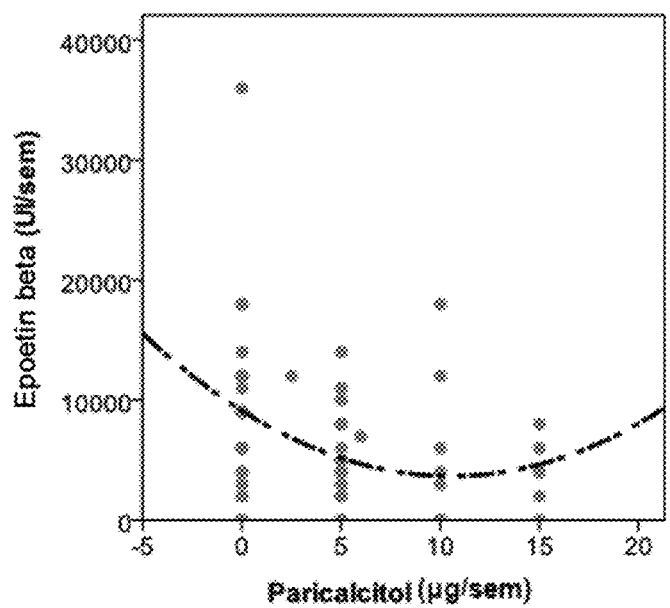
FIG. 2 shows a regression analysis. The graph shows that the dose range of 5-10 µg/week of paricalcitol (x-axis) predicts a greater decrease in the concentration of ESA dose (UI/weel) (y-axis). As of 10 µg/week there is an increase in the ESA doses used (n=58, F=3.65, p=0.03, $R^2$=0.11).

In order to determine the most adequate doses required to obtain the best Hb levels and reduce the need for ESAs, a regression analysis was performed between the Hb levels, the doses of ESAs and the dose of paricalcitol in the group of patients of Study C (FIG. 2). As can be observed in said FIG. 2, the doses comprised between 5 and 10 μg were associated to a reduced need for ESAs. This trend was modified on increasing the doses of paricalcitol, due to which, according to this regression model, the administration of doses of paricalcitol higher than 10 μg/week predicts a greater use of ESAs.

Figure 3:
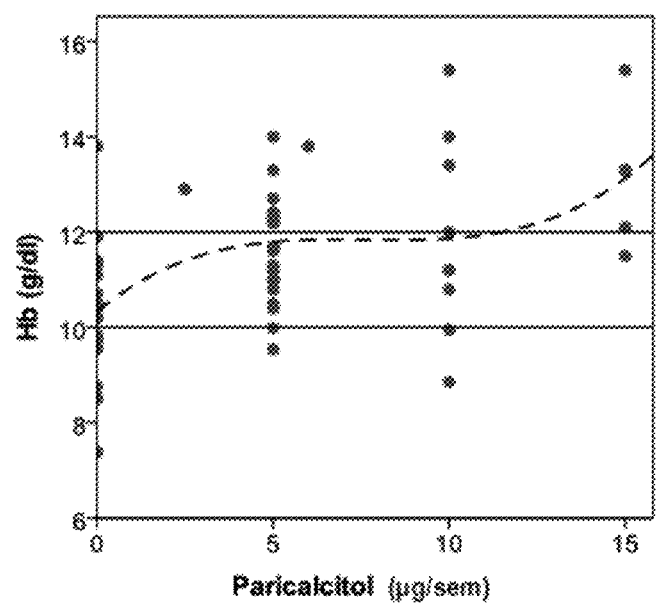
FIG. 3 shows a regression analysis. The graph shows how the doses comprised between 5-10 µg/week of paricalcitol predict plasma Hb levels within a range between 10-12 g/dl. The concentration of paricalcitol (µg/week) is shown on the x-axis and the concentration of Hb (g/dl) is shown on the y-axis (n=58, P<0.01, F=6.952, $R^2$=0.27).

On analysing the relationships between the doses of paricalcitol and Hb levels, the regression analysis reveals that, in the range of doses comprised between 5 and 10 μg/week, Hb levels stood between 10 and 12 g/dl (FIG. 3), values considered to be optimum for the Hb levels in this group of patients (Study C) resulting from the need or not for ESAs.

Therefore, the optimum doses of paricalcitol for obtaining ideal plasma Hb levels between 10 and 12 g/dl, accompanied by less need for ESA in the treatment of patients with inflammatory anaemia, are in the range comprised between 5 and 10 μg/week.

Additionally, the probability of having Hb levels higher than 10g/dl was assessed in the group of patients included in Study C which, according to current guidelines, can be considered a level in which the administration of ESAs is not required, observing that the possibility of presenting Hb levels higher than or equal to 10g/dl is six times greater in patients receiving combined treatment (ESA+PRC) versus those being treated exclusively with ESA (73% versus 27%, p<0.01, $X^2$: 7.91, OR: 6.1 (IC 95%: 1.6-23.38).

Furthermore, on analysing the group of patients receiving combined treatment (ESA+PRC) (Study A), a significant association was observed in said group in relation to higher Hb levels, compared to the group of patients who were being treated exclusively with ESA. Additionally, said benefit was observed despite having received 45% less doses of ESA, as shown in Tables 1 and 4.

TABLE 4

Hb levels in patients receiving combined treatment (ESA + PRC) compared to patients treated exclusively with ESA.

|  | ESA + PRC (n = 19) | ESA (n = 27) | p-value |
|---|---|---|---|
| Hb (g/dl) | 11.5 ± 1.2 | 10.9 ± 1.3 | P = 0.005* |
| ESA dose (UI/week) | 5000 (4000-8000) | 9000 (4000-12000) | 0.07** |

*Student T-Test,
**Mann-Whitney U-Test,
ESA: Erythropoietic-Stimulating Agent,
PRC: Paricalcitol.

Paricalcitol was administered to dialysis patients one to three times a week, as with the administration of the specific ESA used, due to which joint administration would not create difficulties or changes in the usual treatment regimes of these patients. The dose range of paricalcitol includes doses of 5 µg/week. These doses would allow their use in patients with anaemia without CKD, due to the improved profile presented by paricalcitol compared to other agonists of Vitamin D, such as calcitriol, with respect to calcium-phosphorus metabolism, and also because an oversuppression of PHT hormone levels associated with the production of a dynamic bone disease would not occur, which would be an important safety aspect for the administration of paricalcitol. That is, the dose range proposed by the present invention can be used safely both in patients with CKD and secondary hyperparathyroidism, and in patients without CKD or secondary hyperparathyroidism, exclusively presenting inflammatory anaemia.

Comparative Analysis Between Paricalcitol and Calcitriol (Study B).

In order to determine whether treatment with calcitriol is capable of giving rise to the same results obtained in the treatment with paricalcitol, the groups of patients included in Study B were analysed (Table 2), one of the groups treated with paricalcitol (n=61) and the other group treated with calcitriol (n=31).

Figure 4:
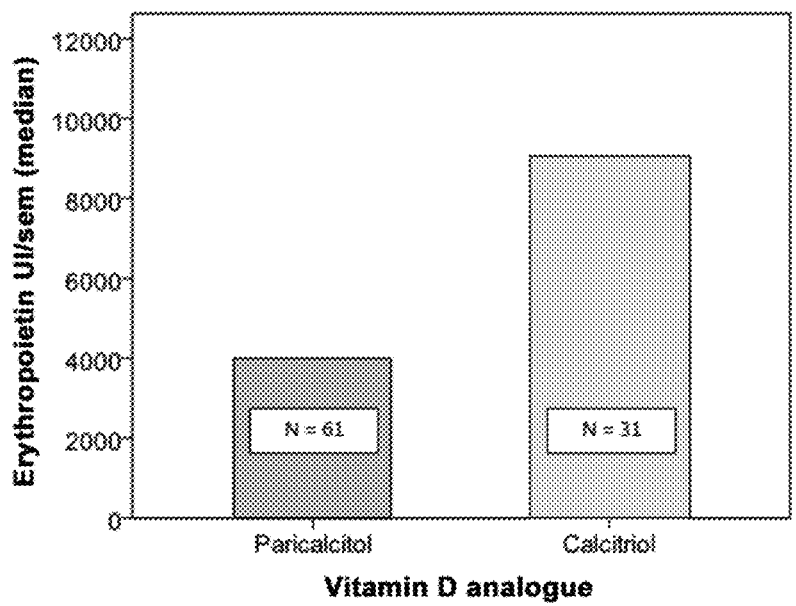
FIG. 4 shows the analysis of ESA requirements in the groups of patients treated with paricalcitol or with calcitriol for treating secondary hyperparathyroidism (p=0.002).

As clearly shown in FIG. 4, the group of patients treated with paricalcitol requires ESA doses of approximately 4000 UI/week, while the group of patients treated with calcitriol required 9000 UI/week, to control secondary hyperparathyroidism (p=0.002. Mann-Whitney Test).

Figure 5:
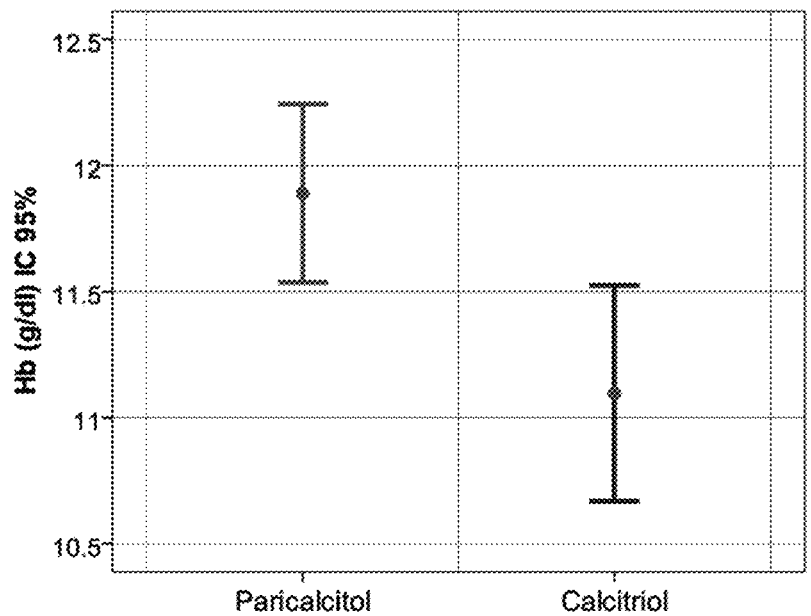
FIG. 5 shows the analysis of Hb levels (g/dl) in patients treated with paricalcitol or calcitriol. The figure reveals the existence of higher levels of Hb in the group of patients treated with (11.89±0.13 g/dl) with respect to the group treated with calcitriol (11.10±1.16 g/dl) (p=0.007).

Additionally, the association of Hb levels between the two groups of patients was also analysed (paricalcitol versus calcitriol) and, as can be observed in FIG. 5, the group of patients treated with paricalcitol showed higher Hb levels (11.89±0.13) with respect to the group of patients treated with calcitriol (11.10±1.16) (p=0.007).

Therefore, these results reveal that the use of paricalcitol is associated to a reduced need for ESAs compared to the use of calcitriol. An association between the use of paricalcitol and higher Hb levels can also be observed, while average Hb levels in those patients being treated with calcitriol were significantly lower. Significant differences in the degree of secondary hyperparathyroidism were not observed between the two groups; however, those patients being treated with paricalcitol had higher levels of TSI (%) despite receiving lower doses of intravenous Fe at the time of the study, as shown in the following table (Table 5):

TABLE 5

|  | Paricacitol (n = 61) | Calcitriol (n = 31) | p-value |
|---|---|---|---|
| PTHi (pg/ml) | 276 (170-449) | 358 (230-623) | 0.18 |
| Ferritin (ng/ml) | 494 (244-701) | 168 (111-298) | <0.01 |

TABLE 5-continued

|  | Paricacitol (n = 61) | Calcitriol (n = 31) | p-value |
|---|---|---|---|
| TSI % | 30 ± 10 | 24 ± 10 | <0.01 |
| IV Fe supplements (mg/month) | 50 (25-63) | 75 (50-100) | <0.01 |

PTHi: Parathormona intacta,
TSI: Transferrin Saturation Index.

These results demonstrate the differences between the two Vitamin D analogues, where paricalcitol presented an improved profile both in terms of ESA requirements, with higher Hb levels, and an improved ferrokinetic pattern than calcitriol.

Analysis of ESA Requirements in the Group of Patients Receiving Combined Treatment and in the Group of Patients Being Treated Exclusively with ESA (Study A).

The data obtained belong to the MIR-EPO study (Study A), previously described in detail (Table 1).

The percentage change in the doses of ESAs in the 31 patients included in the study for months 3 and 6 was: 94±8% (76-112%) and 93±11% (69-116%) (p=0.87), respectively, results that demonstrate that said patients were stable in relation to the doses of ESAs administered.

Figure 6:
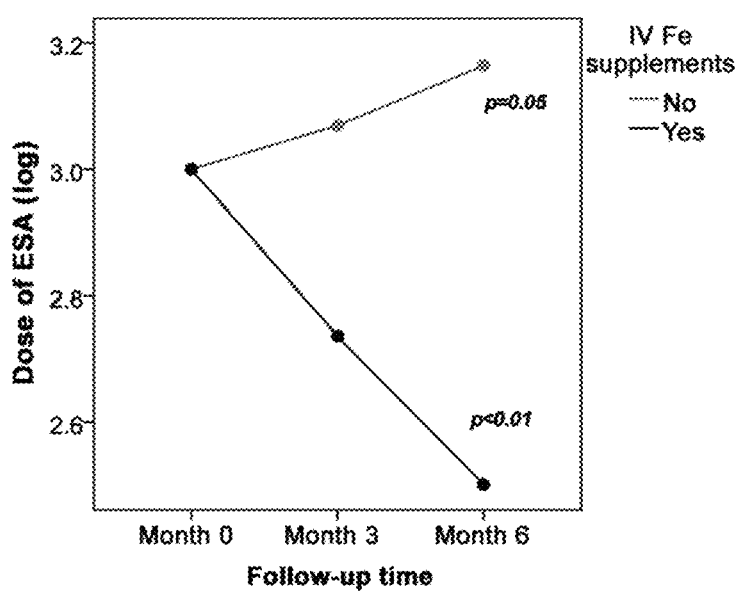
FIG. 6 shows the analysis of the variation in ESA requirements depending on the use or not of IV Fe (intravenous iron) supplements. Increased dose of ESA in the group without IV Fe supplements (p=0.05, F=3.935, partial $Eta^2$: 0.44, n=6) (grey line) compared to decreased dose of ESA in the group with IV Fe supplements (p<0.01, F=5.783, partial $Eta^2$: 0.19, n=25) (black line). The follow-up time expressed in months is shown on the x-axis and the logarithmic expression of the percentage dose of ESA is shown on the y-axis.

The intravenous supplementation of iron (IV $Fe^{2+}$) as the main predictor of the need for erythropoietic agents showed an average decrease in the dose of ESA of 36±14% (IC 95%: 5-66%) (p=0.02) (FIG. 6).

Figure 7:
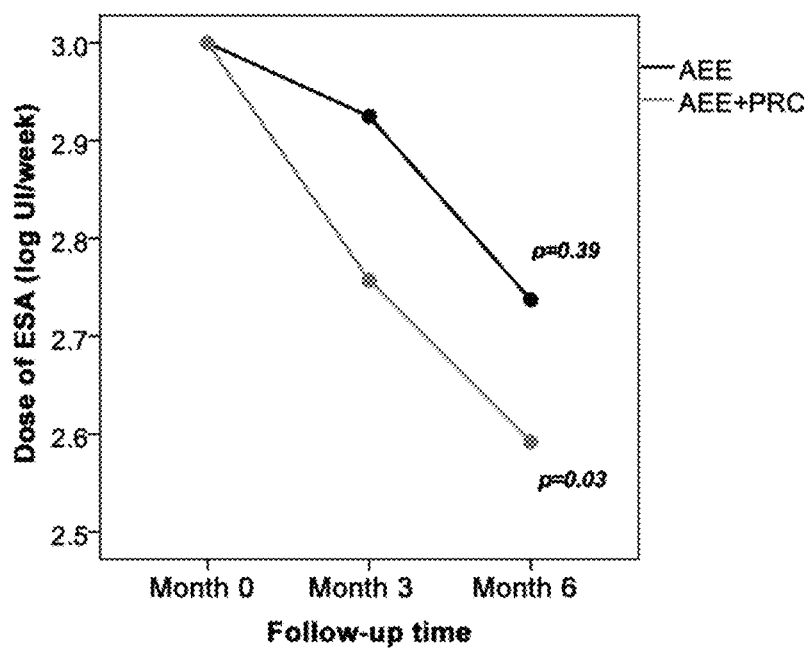
FIG. 7 shows the analysis of ESA dose requirements in the groups of patients treated without paricalcitol (ESA group, black line) and with paricalcitol (ESA group+PRC, grey line). The graph shows the reduction in ESA requirements in the group of patients being treated with paricalcitol (grey line) (n=18, p=0.01, F=4.89, $Eta^2$ parcial: 0.22) compared to the group of patients treated without paricalcitol (black line) (n=8; p=0.39, F=1.09, $Eta^2$ parcial: 0.26). The follow-up time expressed in months is shown on the x-axis and the logarithmic expression of the dose of ESA is shown on the y-axis.

The comparative analysis of the evolution of ESA requirements among the group of patients treated with and without paricalcitol revealed a significant decrease in the group with paricalcitol (n=18, p=0.01, F=4.89, partial $Eta^2$: 0.22) with respect to the group of patients treated with paricalcitol (n=8; p=0.39, F=1.09, partial $Eta^2$: 0.26) (FIG. 7).

Figure 8:
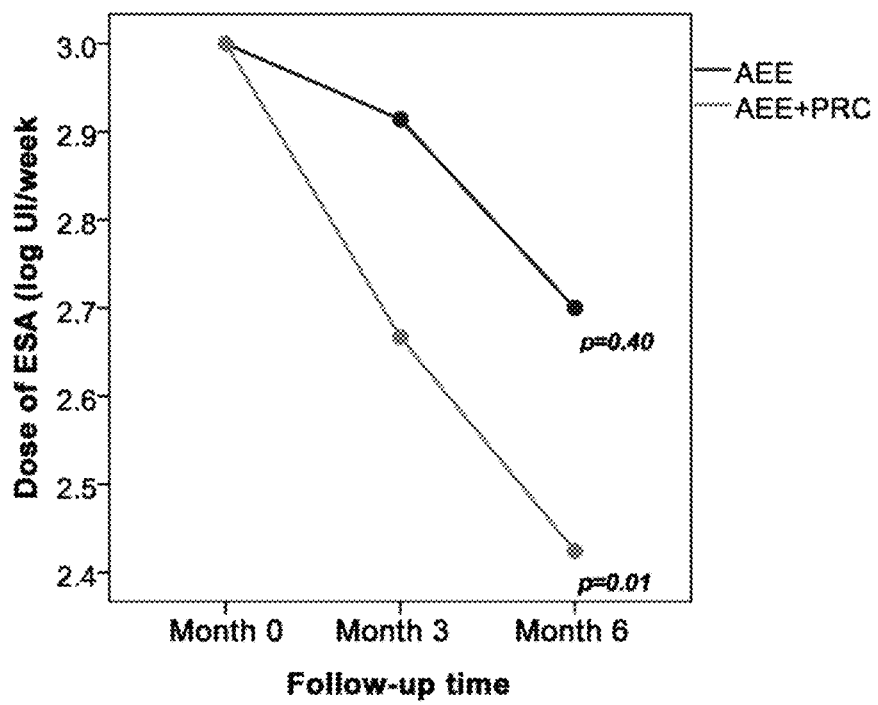
FIG. 8 shows the analysis of ESA dose requirements in the subgroup of patients being treated with IV Fe (n=25). In the group of patients being treated exclusively with ESA supplemented with IV Fe (n=7), a reduction in the required dose of AE was objectified from: 3.00±0.0 to 2.91±0.05 and 2.70±0.28 (% dose, log) (F=1.09, p=0.40, partial Eta$^2$: 0.30) compared to the group of patients treated with ESA+PRC and supplemented with IV Fe (n=18): 3.00±0.0 to 2.66±0.18 and 2.42±0.21 (F=4.891, p=0.01, partial Eta$^2$: 0.22). The average difference in month 6 of the treatment between the two groups corresponds to 24% of the dose of ESA.

In order to determine whether the variations in ESA are independent of treatment with iron ($Fe^{2+}$), the analysis of the evolution of ESA needs in the subgroup of patients that received intravenous supplements of Fe (IV Fe) (n=25) was repeated. The results obtained reveal that, in month 6 of the study, the group of patients being treated with paricalcitol used a 24% lower dose of ESA (FIG. 8). Therefore, the subgroup being treated with ESA (n=7) showed a decrease in the dose from: 3.00±0.0 to 2.91±0.05 and 2.70±0.28 (UI/week, log) (F=1.09, p=0.40, partial $Eta^2$: 0.30) during the study compared to the subgroup receiving combined treatment with ESA+PRC (n=18): 3.00±0.0 to 2.66±0.18 and 2.42±0.21 (F=4.891, p=0.01, partial $Eta^2$: 0.22).

Analysis of the Evolution of the Transferrin Saturation Index (TSI) (Study A).

The evolution in average TSI levels (%) during the study in the patients included in Study A was: 30.5±15, 30.0±13 and 29±17 in months 0, 3 and 6, respectively.

Figure 9:
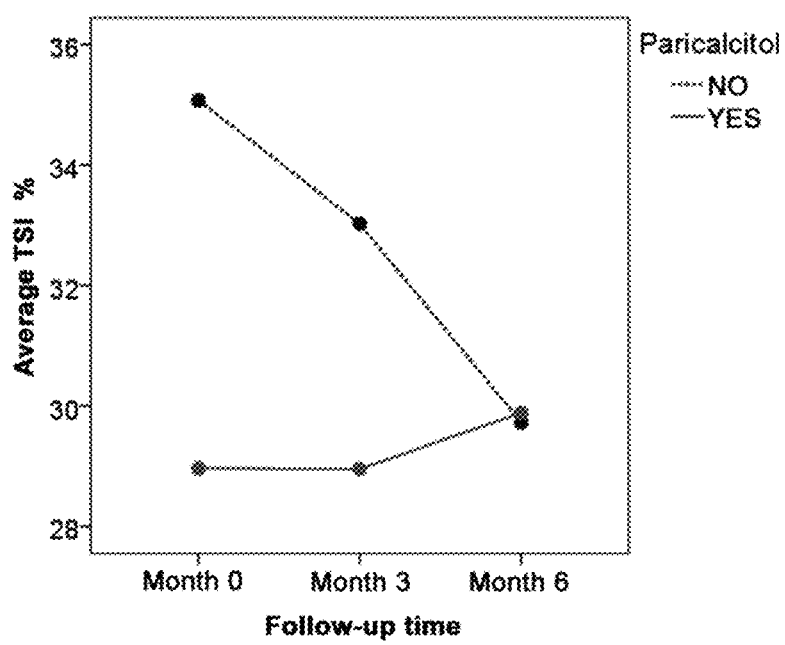
FIG. 9 shows the evolution of TSI levels (expressed as a %) in the group of patients treated with ESA without paricalcitol (ESA, dashed line) during months 0, 3 and 6 of the study: 35.0±6.5, 33.0±5.2 and 29.7±3.2 (F=1.849, p=0.23) and those receiving combined treatment (ESA+PRC; continuous line): 28.9±2.4, 28.9±2.4 and 29.8±3.9 (F=0.021, p=0.98).

On analysing the evolution between the two groups of patients, with and without paricalcitol, it can be observed that the TSI levels were higher in patients of the group treated without paricalcitol (FIG. 9).

Figure 10:
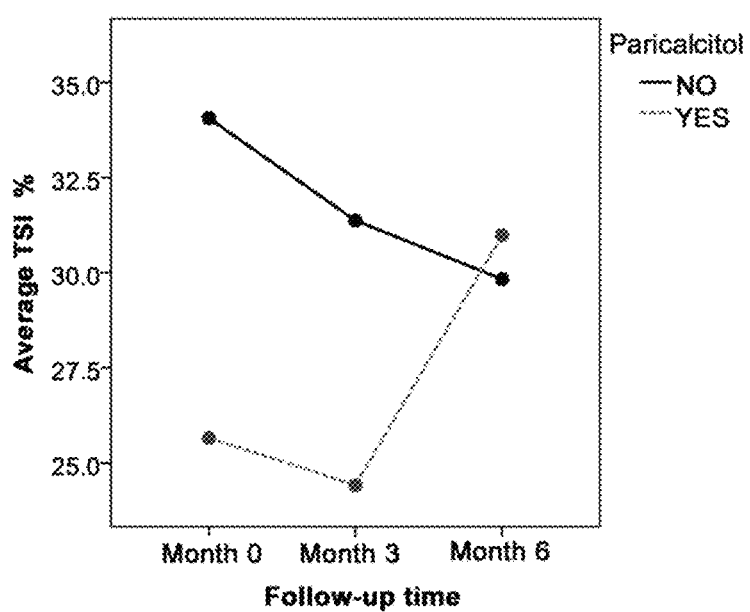
FIG. 10 shows the evolution of the TSI levels (expressed as a %) in the group of patients being treated with intravenous Fe (IV Fe) (n=25) and being treated (discontinuous line) or not (continuous line) with paricalcitol for six months with measurements of said levels at the beginning of the study (month 0), in month 3 and at the end of the study (month 6).

After verifying that the non-administration of iron was associated with a decrease in TSI levels and in order to independently determine iron absorption in the behaviour of TSI levels between the group of patients with and without paricalcitol, the evolution in TSI levels between the two groups, including those being treated exclusively with IV Fe, was assessed (n=25). The results demonstrated that the group without paricalcitol showed lower TSI levels at the end of the study compared to the levels shown at the beginning of the study, whereas the group with paricalcitol showed higher TSI levels at the end of the study compared to the levels at the beginning of the study (FIG. 10). As can be observed in said FIG. 10, average TSI (%) in months 0, 3 and 6 in the group of patients treated without paricalcitol (n=7) was 34±19, 31±15 and 29±9 (F=1.05, p=0.41) and in the group of patients treated with paricalcitol (n=18) was 25±6, 24±5 and 30±19 (F=0.92, p=0.41), respectively.

Figure 11:
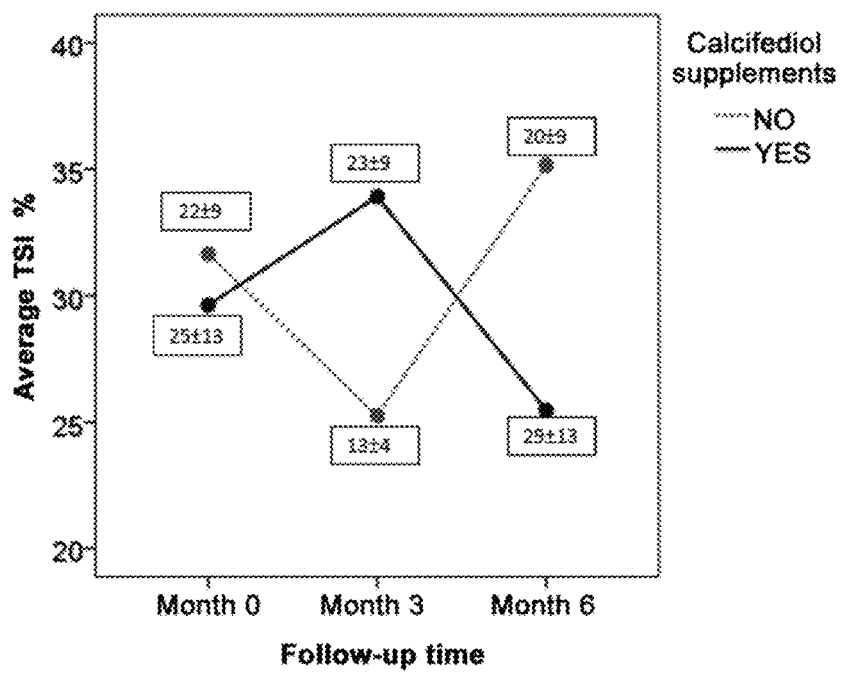
FIG. 11 shows the evolution of the TSI levels (expressed as a %) related to the treatment (continuous line) or not (discontinuous line) with Hidroferol (calcifediol) of increased 25 Vitamin D levels (the numbers that appear in the boxes refer to 25 (OH) vitamin D levels, expressed as ng/ml).

It should be noted that a Vitamin D deficiency is associated with the risk of anaemia, due to which it is presupposed that supplementation with Vitamin D or analogues thereof, could be associated with clear beneficial effects; however, it was observed that the effect of hidroferol (calcifediol), the biologically active form of Vitamin D is not beneficial over TSI. In addition, it was observed that patients being treated with calcifediol presented lower TSI levels at the end of the study (6 months) (FIG. 11). As can be observed in said FIG. 11, there is significant variation in TSI levels (%) in the group of patients treated with hidroferol: 29±12, 33±14 and 25±9 (F=3.33, p=0.04, partial Eta$^2$: 0.17) compared to the group of patients without hidroferol: 31±15, 25±8 and 35±22 (F=1.38, p=0.26, partial Eta$^2$: 0.09). The explanation would be a defect of intestinal iron absorption, due to the absorption of calcium produced by Vitamin D. It was observed that the higher levels of 25(OH)vitamin D are associated with lower TSI values (%) (FIG. 11). This physiological characteristic could be shared by calcitriol, which would partially explain that observed in the comparative study between paricalcitol and calcitriol (Study B). However, this undesirable effect on TSI would be controlled in the case of the use of paricalcitol, as its chemical structure confers lower intestinal $Ca^{2+}$ absorption capacity, thereby avoiding the decrease in intestinal iron absorption.

Analysis of the Evolution of Iron Levels in the Group of Patients Receiving Combined Treatment (ESA+PRC) with Respect to the Group of Patients Treated Exclusively with ESA (Study A).

Iron ($Fe^{2+}$) levels in months 0, 3 and 6 of the study were: 70±28, 68±30 and 65±32 µg/dl (F=0.21, p=0.80). In the analysis between the group with and without paricalcitol, it was observed that the group without paricalcitol (n=8) presented the following average values: 78±40, 70±36 and 64±18 µg/dl (F=2.82, p=0.13) and in the group with paricalcitol (n=23): 68±23, 68±28 and 66±37 µg/dl (F=0.01, p=0.98).

Figure 12:
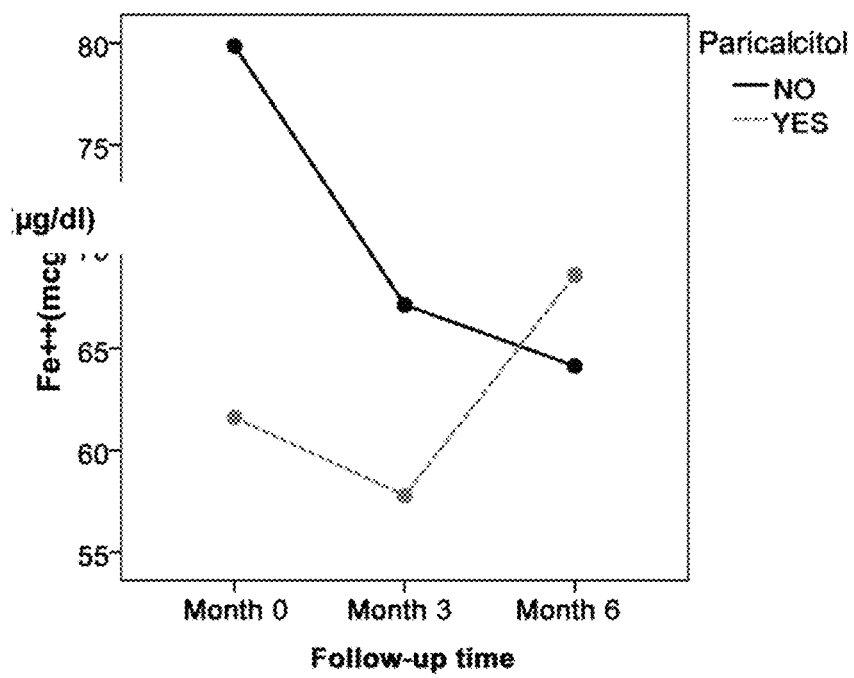
FIG. 12 shows the evolution of Fe2+ levels throughout the study in the subgroup of patients being treated with IV Fe supplements (n=25) and with (discontinuous line) or not (continuous line) with paricalcitol. The follow-up time expressed in months is shown on the x-axis and the concentration of plasma iron (pg/dl) is shown on the y-axis.

The analysis of the evolution of the $Fe^{2+}$ levels among patients being treated with IV Fe supplements (n=25), both belonging to the group without or with paricalcitol, is shown in FIG. 12. As can be observed in said FIG. 12, the analysis between the subgroup of patients undergoing treatment without paricalcitol (n=7) presented the following average values: 79±43, 67±37 and 64±20 µg/dl (F=2-03, p=0.22) and the group with paricalcitol (n=18): 61±16, 57±14, 68±37 µg/dl (F=0.80, p=0.46).

Integrating the results, it can be concluded that, although the general average showed a downward trend in plasma $Fe^{2+}$ levels, this decrease is determined by the decrease presented in those patients not being treated with paricalcitol. Therefore, the increase in $Fe^{2+}$ in those patients being treated with paricalcitol that can be observed at the end of the study would explain the increase in TSI (%) observed in this subgroup, as $Fe^{2+}$ has a positive correlation with TSI (%).

Analysis of the Evolution in Plasma Ferritin Levels (Study A).

Figure 13:
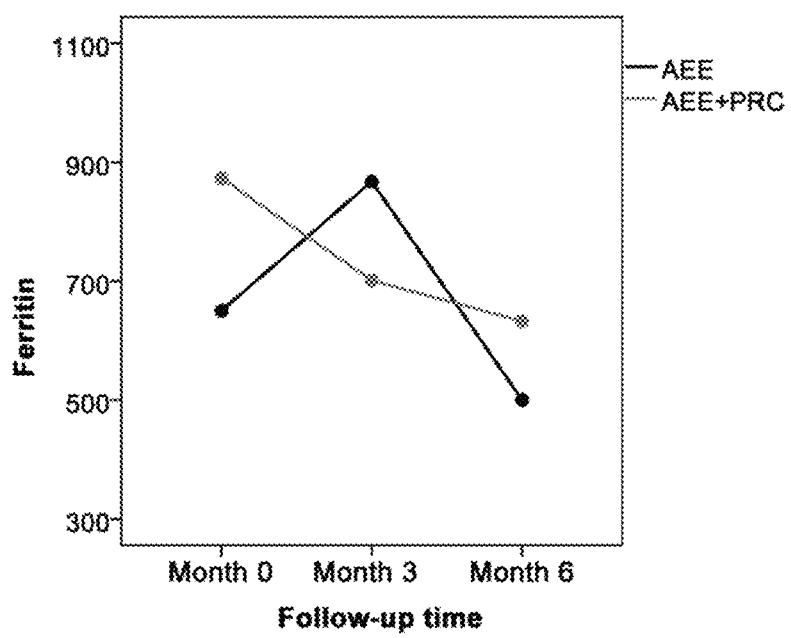
FIG. 13 shows the evolution of the plasma iron levels (ng/ml) throughout the study. A progressive linear reduction can be observed in those patients receiving combined treatment (ESA+PRC, grey line): 873±102, 701±81 and 632±69 (ng/ml) (F=8.294, p<0.01, partial Eta$^2$: 0.44), while in those patients treated exclusively with ESA (black line) an increase in said levels was observed in month 3 and a dramatic decrease in month 6: 650±131, 876±197 and 500±96 (ng/ml) (F=3.370, p=0.06, partial Eta$^2$: 0.32).

The results shown in the group of patients included in Study A reveal a decrease in iron deposits throughout the study, presenting the following values: 815±469, 744±435 and 598±320 ng/ml (F=5.63, p<0.01, partial Eta$^2$: 0.15) in months 0, 3 and 6, respectively. The decrease in ferritin levels was also observed on analysing the group of patients being treated exclusively with ESA (n=8) (650±373, 867±558 and 500±271 (ng/ml), F=8.65, p=0.01, partial Eta$^2$: 0.74), in the same manner as in the group of patients receiving combined treatment (ESA+PRC) (n=23), presenting the following average values for months 0, 3 and 6: 873±492, 701±389 and 632±334 (ng/ml), F=8.29, p<0.01, partial Eta$^2$: 0.41) (FIG. 13).

Analysis of the Expression of Different Inflammatory Markers (Study A).

Evolution in Interleuquina-6 (IL-6) levels.

IL-6 levels (pg/ml, log) did not vary throughout the study (0.89±0.46 and 0.91±0.83; p=0.83, F=0.04).

The comparative analysis between groups receiving combined treatment (ESA+PRC) versus those being treated exclusively with ESA did not reveal variations during the follow-up time, although the group receiving combined treatment with paricalcitol presented lower levels of this cytokine.

Figure 14:
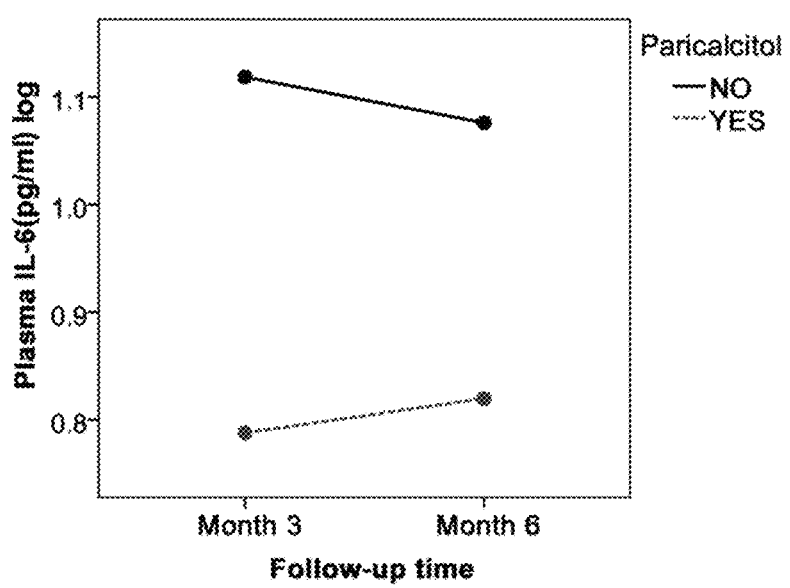
FIG. 14 shows the evolution of IL-6 levels in those patients being treated exclusively with ESA (continuous line) in months 3 and 6 of the study: 1.11±0.19 and 1.07±0.16 (F=3.87, p=0.10) compared to those receiving combined treatment (PRC+ESA, discontinuous line): 0.78±0.11 and 0.82±0.09 (F=0.14, p=0.70). The average levels of IL-6 in those patients with ESA was 1.09±0.15 compared to those receiving combined treatment (PRC+ESA, discontinuous line) 0.80±0.08 (F=2.36 and p=0.13).

As little is known about the factors that influence the evolution of these markers, the statistical model was adjusted according to PTHi and GSV values. The results obtained showed a similar evolution in the two groups, presenting lower IL-6 levels in the group receiving combined treatment (FIG. 14).

Evolution in Hepcidin Levels.

Figure 15:
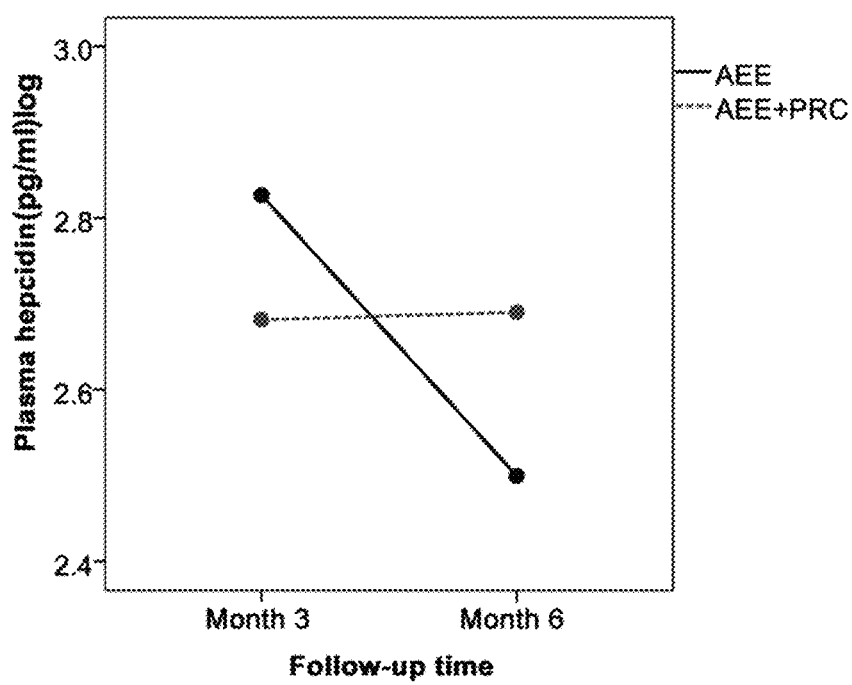
FIG. 15 shows a decrease in benzidine (pg/ml) log) in those patients being treated exclusively with ESA (continuous line): 2.82±0.12 to 2.50±0.16 (p=0.03, F=7.763) compared to those receiving combined treatment (discontinuous line): 2.68±0.17 to 2.69±0.12 (p=0.95, F=0.003).

The average hepcidin values during the study were: 2.72±0.57 versus 2.62±0.45 µg/ml, log (F=0.67, p=0.42). In the group of patients without paricalcitol, a decrease in hepcidin levels were observed at the end of the study (2.82±0.12 versus 2.50±0.16 pg/ml, log, p=0.03, F=7.76) and in patients with paricalcitol the evolution was 2.62±0.17 versus 2.69±0.12, p=0.95, F=0.00). Significant differences in the average values of this pro-inflammatory marker between the two groups were not observed (ESA versus PRC+ESA: 2.66±0.16 versus 2.68±0.11 pg/ml, log (p=0.91) (FIG. 15).

Figure 16:
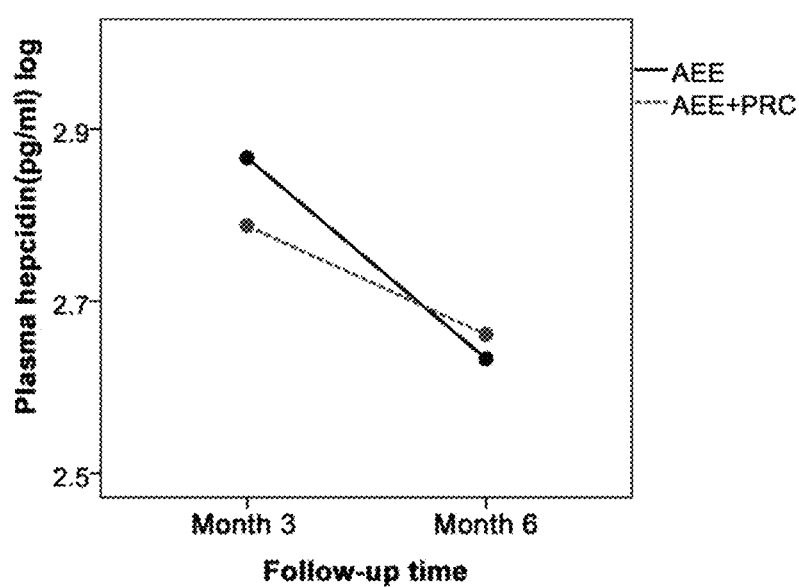
FIG. 16 shows the evolution of Hepcidin levels (pg/ml (log)) in a model adjusted according to PTHi (parathormona intacta) and GSV (globular sedimentation velocity) levels for the group of patients receiving combined treatment (ESA+PRC, discontinuous line): 2.80±0.12 to 2.72±0.12 (p=0.54, F=0.38) compared to those being treated exclusively with ESA (continuous line): 2.82±0.11 to 2.50±0.17 (p=0.24, F=1.827).
Figure 17:
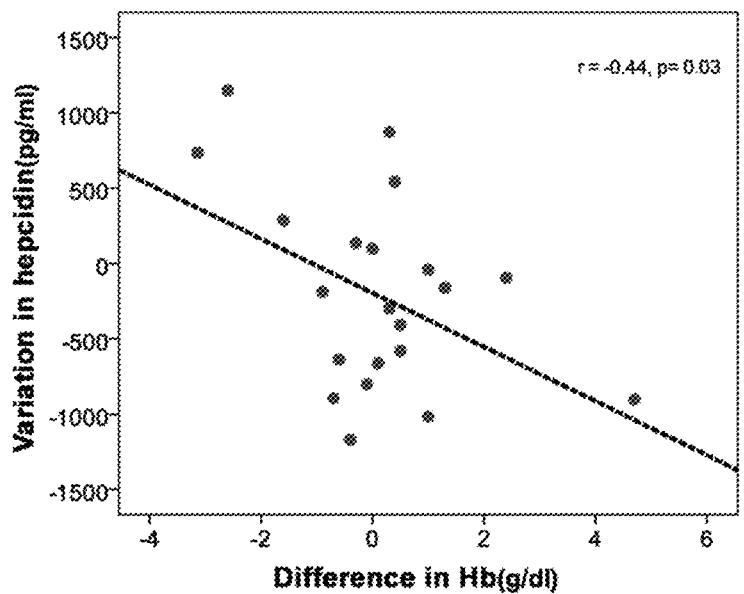
FIG. 17 shows a correlation analysis between the hepcidin levels (pg/ml) and Hb levels (g/dl) during months 3 to 6 of the study.
Figure 18:
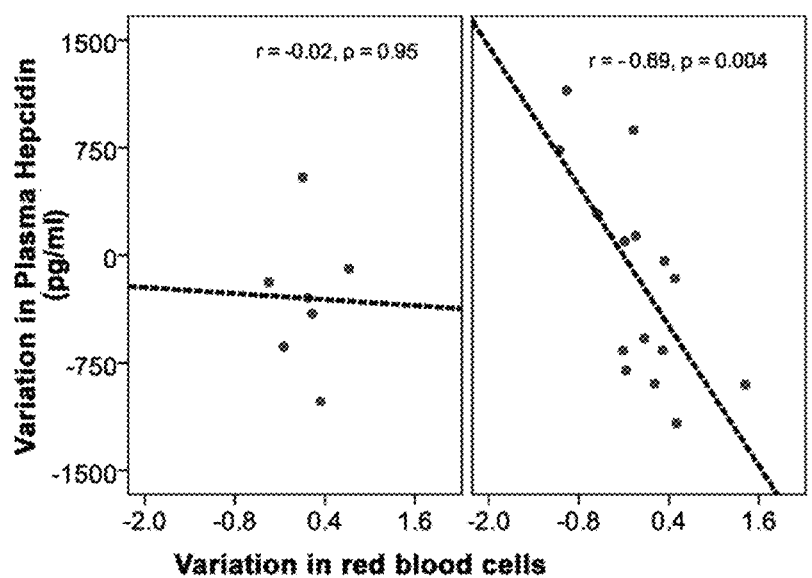
FIG. 18 shows a correlation analysis between the group of patients being treated with ESA (graph on the left) compared to those receiving combined treatment (ESA+PRC) (graph on the right) between the variation in red blood cell levels (M/ul) and plasma hepcidin levels (pg/ml).

On performing the comparative analysis adjusted according to PTHi and GSV levels, it was observed that the average values of plasma hepcidin in months 3 and 6 of the study, evolved in a similar manner in the group of patients treated with ESA and in the group treated with ESA+PRC (FIG. 16). The similar evolution of this parameter in the two treatment groups, in months 3 and 6 of the study, taking into account that said phase of the study is considered to be the maintenance phase, it is important due to the fact that the evolution of hepcidin levels during said maintenance phase (month 3 to month 6) is inversely correlated with the variation observed in haemoglobin levels (FIG. 17). Said inverse correlation is also observed in the evolution of the number of red blood cells in the group receiving paricalcitol; however, this correlation was not presented in the group of patients that did not receive paricalcitol (FIG. 18).

Figure 19:
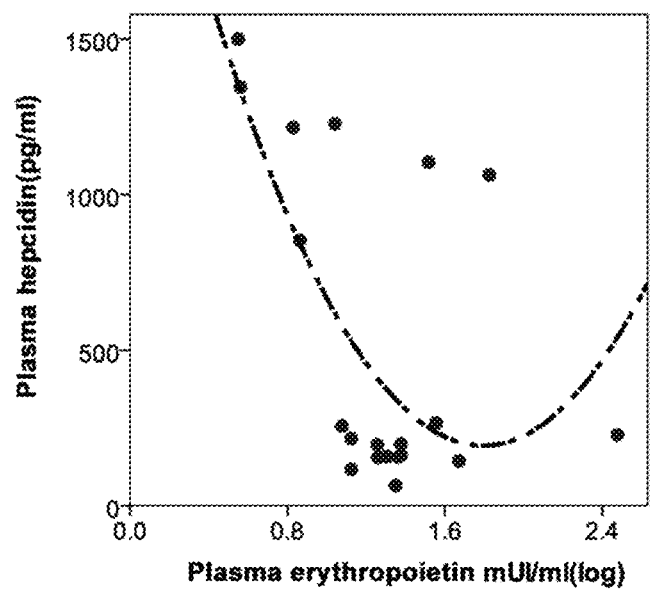
FIG. 19 shows a regression analysis. Quadratic regression curve between the hepcidin levels (pg/ml) (y-axis) and plasma erythropoietin levels (mUI/ml) log) (x-axis) (F=6.66, p<0.01, R$^2$: 0.44 (n=20)).

These results confirm the benefit of the treatment with paricalcitol, as the main determining factor of the hepcidin levels is the concentration of plasma erythropoietin, as was observed by means of a regression analysis between hepcidin (pg/ml) and erythropoietin (mU/ml) (log) levels performed at the end of the study (FIG. 19).

Additionally, this study reveals that hepcidin levels decreased in a similar manner both in patients treated exclusively with ESA and in patients receiving combined treatment (ESA+PRC), despite the fact that the latter received a lower dose of ESA. It is also interesting to note that, in the group of patients receiving combined treatment, the decrease in hepcidin levels is correlated with higher Hb levels, which represents an adequate physiological response.

Furthermore, the present invention shows how the hepcidin levels are directly associated with the ferritin levels (in patients receiving combined treatment (r=0.55, p=0.03), due to which the decrease in ferritin levels arising from a combined treatment, not based on high doses of ESA, would have a different effect of the combined treatment, not described until now in the state of the art, that lies in the reduced tissue overload of $Fe^{2++}$ (giving rise to the high plasma ferritin levels), thereby avoiding its related adverse effects (García-Yébenesl, et al., NeurochemInt. 2012 December: 61:1364-9; Gujja P, et al., J Am Coll Cardiol. 2010 September: 56:1001-12).

Evolution of Soluble Plasma Klotho Levels.

The results obtained reveal a significant decrease in Klotho levels throughout the study, presenting average values at month 3 and 6: 2.72±0.14 to 2.66±0.14 pg/ml, log, respectively ($p<0.01$, F=12.74, partial $Eta^2$: 0.31).

Figure 20:
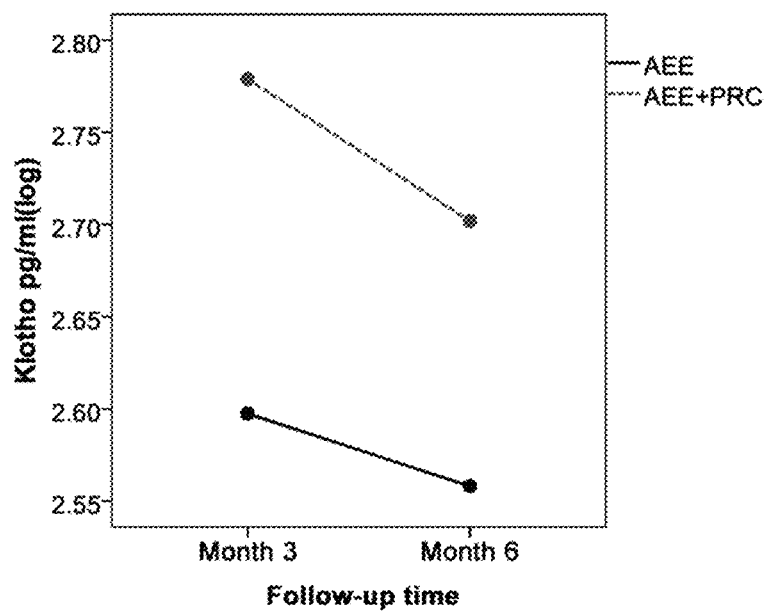
FIG. 20 shows the evolution of Klotho levels (pg/ml,log) during months 3 and 6 of the study. It can be observed how the Klotho levels are higher during the follow-up in the group receiving combined treatment (ESA+PRC) (discontinuous line) compared to those being treated exclusively with ESA (continuous line): 2.74±0.02 vs 2.57±0.02 pg/ml (log) (p<0.01, F=11-08, partial Eta$^2$: 0.29).

The comparative analysis between the group of patients treated exclusively with ESA with respect to the group of patients receiving combined treatment, ESA+PRC revealed a decrease in Klotho levels (pg/ml) (log) in the two groups of patients during the follow-up time (between month 3 and 6). Klotho levels in the group receiving combined treatment were: 2.59±0.10 to 2.55±0.09 pg/ml (log) (p=0.22, F=1.77, partial $Eta^2$: 0.20) versus 2.77±0.12 to 2.70±0.14 pg/ml (log) ($p<0.01$, F=11.08, partial $Eta^2$: 0.36) obtained in the group treated exclusively with ESA. However, despite the decrease in the levels of the group of patients without paricalcitol, it was also observed that average Klotho levels were higher in the group receiving combined treatment: 2.74±0.02 versus 2.57±0.02 pg/ml (log) ($p<0.01$, F=11.08, partial $Eta^2$: 0.29) (FIG. 20).

Figure 21:
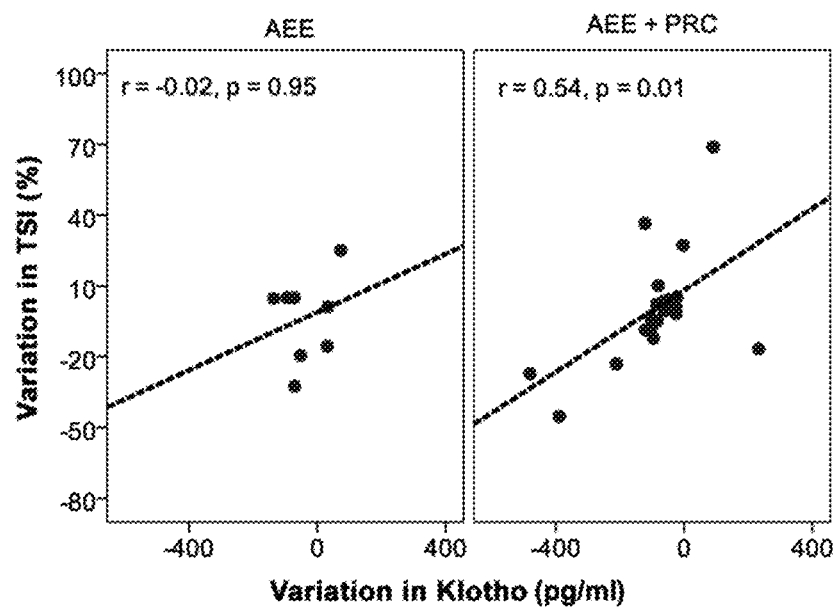
FIG. 21 shows a correlation analysis between the TSI (%) and Klotho (pg/ml) levels. Positive correlation can be observed in the group receiving combined treatment (n=20) (ESA+PRC). Said correlation is not observed in the group being treated exclusively with ESA (n=8). ESA: erythropoiesis-stimulating agent. PRC: paricalcitol.

Furthermore, positive correlation with the evolution of TSI and Klotho values in months 3 and 6 in those patients receiving combined treatment (ESA+PRC) was also revealed, while said correlation was not observed in those patients treated exclusively with ESA (FIG. 21).

A correlation analysis was performed between the evolution of Klotho levels and the presence of free iron between months 3 and 6 of the study, which showed statistical significance in those patients receiving combined treatment ($p<0.01$, r=0.60, n=20) with respect to non-significant correlation in those patients being treated exclusively with ESA (r=0.31, p=0.45, n=8).

Therefore, the results shown demonstrate that the higher plasma Klotho levels in those patients receiving combined treatment are associated to a higher level of free plasma iron and improved TSI (%), which determine a lower rate of red blood cell destruction (inhibition of eryptosis) and, additionally, it would be associated to a greater facility for producing red blood cells at bone marrow level.

Analysis of the Evolution in Plasma Erythropoietin Levels (Study A).

One of the main causes of the development of anaemia in patients with CKD arises from the decrease in secondary erythropoietin levels associated with the deterioration of kidney function. Since the kidney is the main organ responsible for erythropoietin synthesis, the administration of lower doses of erythropoietin would result in a logical decrease in blood plasma levels of this hormone. In the state of the art, the administration of Vitamin D or analogues thereof is related to reduced resistance to erythropoietin; however, it has never been assessed that treatment with said compounds, in addition to reducing ESA requirements, induces an increase in endogenous erythropoietin synthesis.

Figure 22:
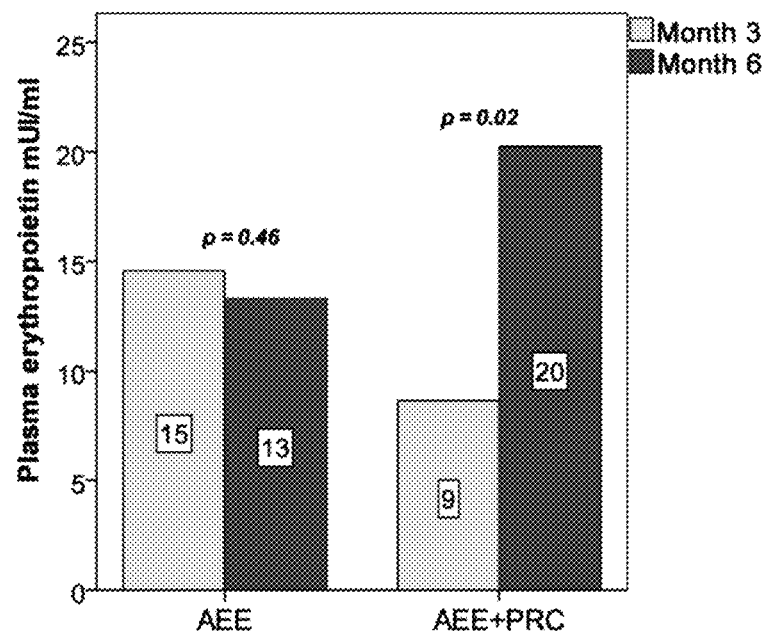
FIG. 22 shows the evolution of plasma erythropoietin levels (mUI/ml) in months 3 and 6 of the study. A significant increase in plasma erythropoietin levels can be observed in the group receiving combined treatment (ESA+PRC) (n=20) compared to a non-significant decrease in the group being treated exclusively with ESA (n=8).

In this connection, the present invention shows an increase in plasma erythropoietin in the group of patients receiving combined treatment (ESA+PRC), with average values in month 3 and 6: 10.1 mUI/ml (4.96-16.8 mUI/ml) and 18.1 mUI/ml (8.2-26.1 mUI/ml) (p=0.01), respectively, with respect to the values obtained in the patients being treated exclusively with ESA (FIG. 22). As observed in said FIG. 22, the average EPO values in the group of patients without paricalcitol from month 3 to 6 were: 14.5 (4.7-19) to 13.3 (10-21) mUI/ml (p=0.46) and in the group with paricalcitol the values increased from 8.6 (4.6-16.7) to 20.2 (7.2-33.6) mUI/ml (p=0.02).

Figure 23:
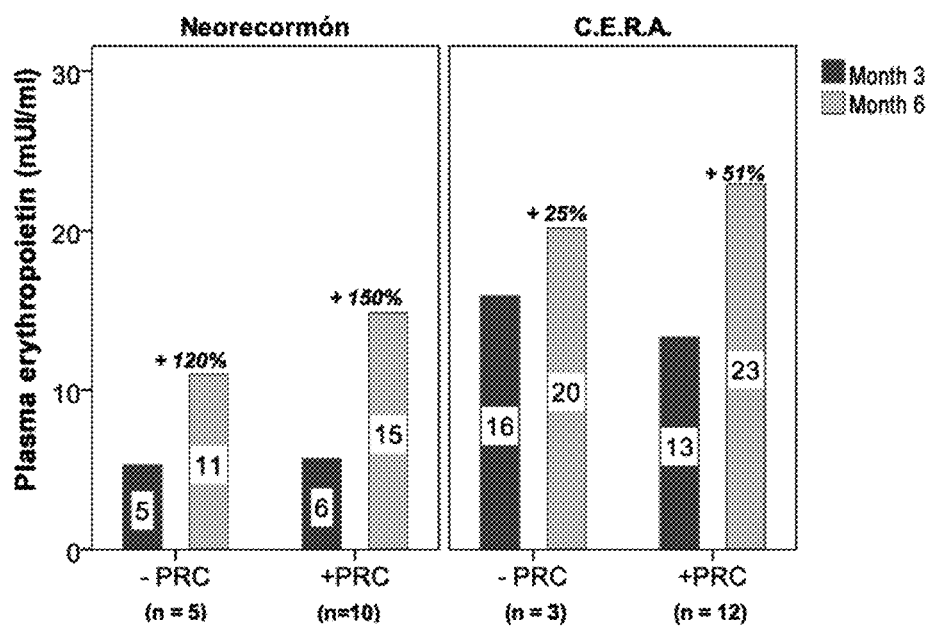
FIG. 23 shows the evolution of median levels of erythropoietin (mUI/ml) according to the type of ESA. It can be observed that the percentage increase in erythropoietin levels is greater in those patients receiving combined treatment with paricalcitol (+PRC), both those being treated with the AAE Neorecormon and those being treated with the ESA CERA.

Due to the fact that, during the study, two different forms of ESA were use, a sub-analysis of the evolutions of erythropoietin levels according to the type of ESA (Neorecormon and CERA) received by each group of patients and in relation to the treatment with or without paricalcitol (FIG. 23), observing that in both groups, joint use with paricalcitol is associated with higher percentage values of plasma erythropoietin levels.

Figure 24:
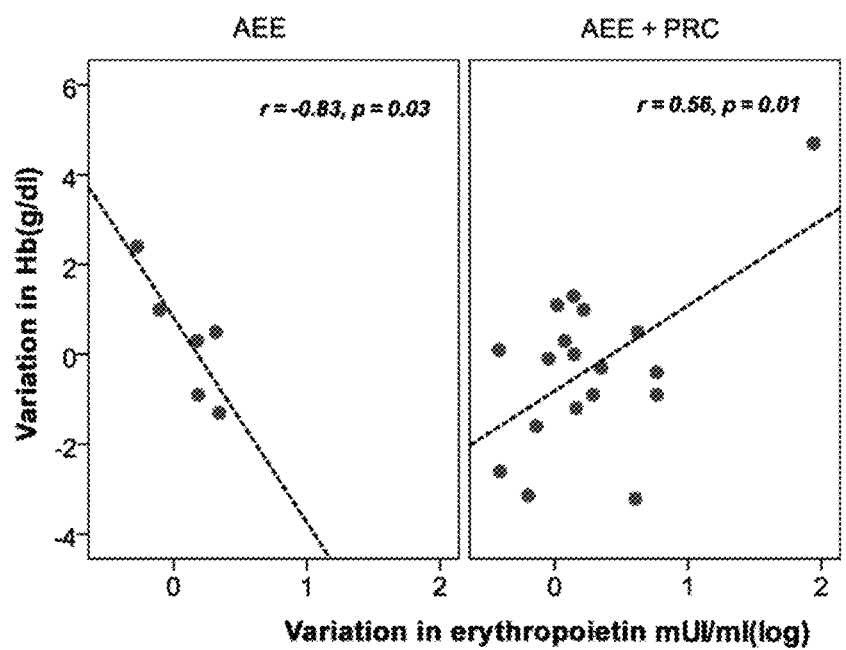
FIG. 24 shows the correlation analysis between plasma erythropoietin (mUI/ml) and haemoglobin (g/dl) levels among the group of patients being treated exclusively with ESA (n=6) versus those receiving combined treatment (ESA+PRC) (n=18).

In order to assess the effect of the increase in plasma erythropoietin levels, a correlation analysis between the variation in plasma erythropoietin levels and the variation in haemoglobin levels was performed, observing that in those patients receiving combined treatment (ESA+PRC) a positive correlation was observed in accordance with the expected physiological response; however, significantly, a negative correlation was observed in the group treated exclusively with ESA, indicating that, possibly, increasing erythropoietin levels by increasing the dose of ESA would not entail an improvement in erythropoietic response (FIG. 24).

Analysis of the Evolution in the IV Fe Doses Between the Group of Patients Treated without and with Paricalcitol (Study A).

Figure 25:
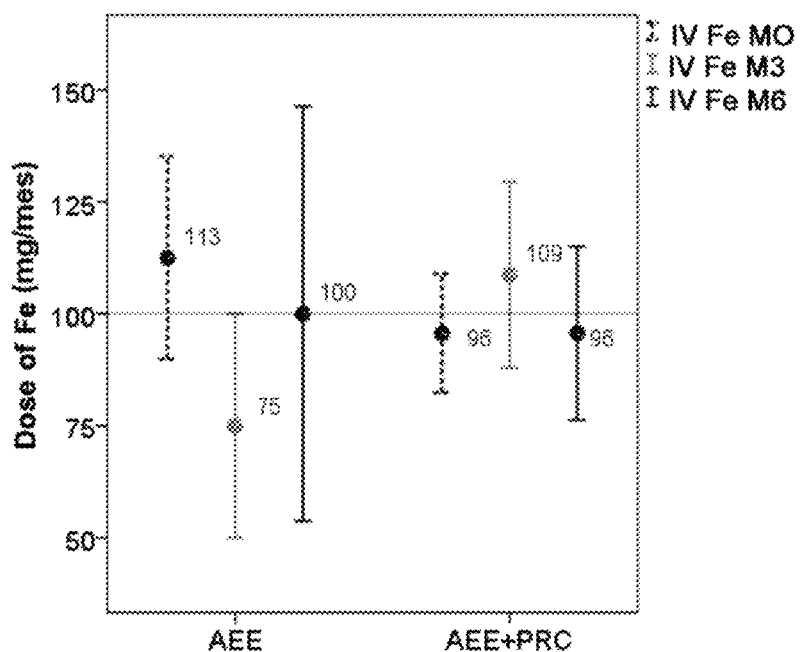
FIG. 25 shows the evolution of the doses of IV Fe supplements (mg/month) among the group of patients receiving combined treatment (ESA+PRC) and in the group of patients being treated exclusively with ESA. The graph shows the values expressed as median±SD.

A variation in the dose of IV Fe was not observed during the study period (FIG. 25). The group without paricalcitol received 113±22 mg, 75±25 and 100±46 mg/week (p=0.20, F=2.091), while the evolution in the group with paricalcitol was 96±13, 109±20 and 96±19 (p=0.64, F=0.43).

Analysis of the Stability in Haemoglobin Levels in the Group of Patients Treated with or without Paricalcitol (Study A).

Figure 26:
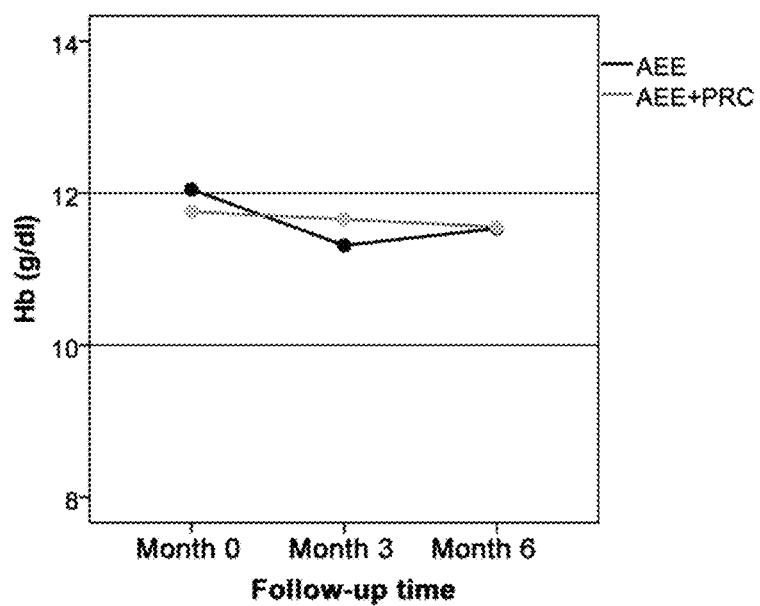
FIG. 26 shows the evolution of Hb levels (g/dl) in the group of patients being treated with ESA (black line) (n=8) in months 0, 3 and 6, respectively: 12.0±0.3, 11.3±0.3 and 11.5±0.3 (g/dl) (p=0.24, F=1.55) compared to those receiving combined treatment (ESA+PRC, grey line): 11.7±0.1, 11.6±0.3 and 11.5±0.2 (g/dl) (p=0.82, F=0.19).

Hb levels throughout the MIR-EPO study (Study A) did not vary significantly, observing that their evolution was different among the group treated with ESA with respect to those receiving combined treatment (ESA+PRC), as can be observed in FIG. 26.

As mentioned earlier, haemoglobin variability is associated with a discreet but higher mortality rate in patients being treated with ESAs. In this connection, Hb level variability was analysed throughout the study in both groups of patients. The results show that this variability is lower in those patients receiving combined treatment with ESA and paricalcitol with respect to those being treated exclusively with ESA (FIG. 27). Said figure reveals that Hb levels between months 0-3 (grey lines) and months 3-6 (black lines) among the group of patients being treated with ESA (n=8) was: 0.73±1.30 and −0.22±1.17 (p=0.25) and in the group of patients receiving combined treatment (n=23): 0.10±0.14 and 0.10±1.70 (p=0.99), between months 0 to 3 and 3 to 6, respectively.

This significant degree of stabilisation in haemoglobin values in the group of patients receiving combined treatment implicitly entails an effect not analysed to date and which would have a special interest in the erythropoietic response. If, as we have observed, the combined use of ESA and paricalcitol is associated to improved Hb levels, the uncontrolled increase in Hb and, obviously, red blood cell levels could generate polyglobulia and hyperviscosity deleterious to health.

On analysing the average variation in Hb levels among those patients receiving combined treatment (ESA plus paricalcitol) versus those being treated with ESA, an inverse linear correlation was observed between the variations comprised between months 0 and 3 and months 3 and 6 ($r=-0.57$, $P=0.004$), i.e. it was observed that those patients who increased their average Hb levels in the third month with respect to month 0 correlatively decreased their average haemoglobin levels between months 3 and 6 of the study.

Therefore, the results reveal that the use of paricalcitol in the group of patients receiving combined treatment produced a stringent control over haemoglobin levels, due to which under this condition, it could be considered that the selective activation of the Vitamin D receptor, as demonstrated in the present invention, through the use of paricalcitol, is indispensable in the treatment of inflammatory anaemia.

All the results shown in the present invention prove that treatment with paricalcitol has a beneficial effect on ferrokinetics, said beneficial effect being associated with the best profile on inflammatory cytokine and hepcidin levels which, in turn, is associated with a better use of tissue iron deposits. Additionally, the lower hepcidin levels are associated with high Hb levels and with higher number of red blood cells, this inverse correlation occurs in those patients being treated with paricalcitol and is consistent with the properties attributed to hepcidin; however, in the data shown in the present invention, correlation is not observed between the decrease in hepcidin levels and the hypothetical increase in the number of red blood cells in patients not being treated with paricalcitol, which suggests a physiological blockage phenomenon in the decrease in hepcidin in this group of patients. It was also observed that TSI decreased despite the increase in the dose of IV Fe which, added to the decrease in plasma ferritin levels, leads us to conclude that greater iron absorption arising from an increased erythropoietic activity due to the higher doses of ESA required by this group of patients with respect to the group being treated with paricalcitol.

Conversely, in the group of patients being treated with paricalcitol, an inverse correlation between hepcidin levels and the number of red blood cells, and an increase in TSI levels, was observed, despite receiving lower doses of IV Fe which, added to the decrease in ferritin levels, indicates the existence of an endogenous iron supply, i.e. an adequate mobilisation of intracellular iron deposits, while maintaining constant plasma haemoglobin levels.

It should also be noted that the hepcidin levels in the group of patients who received paricalcitol presented a similar evolution to the group treated exclusively with ESA, a group that required a higher dose of ESA. This is justified by the increase in erythropoietin levels in those patients who received paricalcitol, due to the fact that, as demonstrated throughout the present invention, it is the level of plasma erythropoietin which induces an inhibition in hepcidin expression levels.

Furthermore, the presence of higher Klotho levels in those patients being treated with paricalcitol could be a new property in the treatment of inflammatory anaemia. It has been described that red blood cells in patients with diseases such as CKD, iron deficiency, erythropoietin deficiency and, at animal experiment level, Klotho deficiency, is associated with a premature death process called eryptosis. It is observed that Klotho levels are positively correlated with the plasma iron levels.

In the comparative analysis of patients receiving combined treatment, there was a direct correlation between the evolution of plasma iron and Klotho levels, whereas this relationship was not observed in the group that did not receive paricalcitol.

The use of ESA showed that the group being treated with paricalcitol required less doses of erythropoietic agents with respect to the group without paricalcitol to maintain similar plasma Hb levels. This effect was independent of the administration of iron supplements, as observed in the study. The determination of plasma erythropoietin levels show how, over time, those patients being treated with paricalcitol, raised their plasma levels. This effect was independent of the administration of ESA and its doses, as precisely in this group of patients the doses administered were lower. The explanation to this phenomenon could be related to a lower elimination of plasma erythropoietin levels or, what seems more likely, with a greater endogenous synthesis thereof.

The evolution of average Hb levels in the group of patients receiving combined treatment showed a very significant stability of said molecule and never described by other treatments, observing a significant inverse correlation between the degree of variation in Hb levels between months 0 and 3 and the variation observed between months 3 and 6 of the study, thereby conferring the treatment with paricalcitol a regulating effect on erythropoiesis.

As can be observed in the results shown in the present invention, in the group of patients that did not receive paricalcitol, the increase in the dose of iron (between month 3 and 6) was not associated to a significant increase in Hb levels or to an increase in TSI; moreover, in light of the results obtained, the increase in the dose of ESA and the consequent increase in plasma erythropoietin levels, may not be associated with an improved response over Hb. It even appears that it could lead to lower haemoglobin levels, due to which the treatment of anaemia in this group of patients is limited due to the less effective treatment thereof. On the contrary, the use of paricalcitol was associated with optimised iron absorption, an increase in erythropoietin levels and an adequate response thereto.

In summary, the anti-inflammatory properties, together with the increase in erythropoietin levels in patients receiving paricalcitol, confer it an interesting role as an adjunct therapy in patients with anaemia of inflammatory characteristics, as a consequence of optimised iron absorption and the decrease in erythropoietic agent requirements.

The invention claimed is:

1. A method of inducing an increase of endogenous erythropoietin synthesis in patients in dialysis suffering from inflammatory anemia said method comprising administering paricalcitol to a subject, wherein the dose of paricalcitol to be administered is between 5-10 μg/week.

* * * * *